US011170898B2

(12) United States Patent
Neumann

(10) Patent No.: US 11,170,898 B2
(45) Date of Patent: Nov. 9, 2021

(54) METHODS AND SYSTEMS FOR PRIORITIZING USER SYMPTOM COMPLAINT INPUTS

(71) Applicant: KPN INNOVATIONS, LLC, Lakewood, CO (US)

(72) Inventor: Kenneth Neumann, Lakewood, CO (US)

(73) Assignee: KPN INNOVATIONS, LLC, Lakewood, CO (US)

( * ) Notice: Subject to any disclaimer, the term of this patent is extended or adjusted under 35 U.S.C. 154(b) by 0 days.

(21) Appl. No.: 16/589,050

(22) Filed: Sep. 30, 2019

(65) Prior Publication Data

US 2021/0098128 A1 Apr. 1, 2021

(51) Int. Cl.
  *G16H 50/20* (2018.01)
  *G16H 50/70* (2018.01)
  *G06N 20/10* (2019.01)
  *G06K 9/62* (2006.01)

(52) U.S. Cl.
  CPC ............ *G16H 50/20* (2018.01); *G06K 9/623* (2013.01); *G06K 9/6256* (2013.01); *G06K 9/6276* (2013.01); *G06N 20/10* (2019.01); *G16H 50/70* (2018.01)

(58) Field of Classification Search
  CPC .................................................. G16H 50/20
  See application file for complete search history.

(56) References Cited

U.S. PATENT DOCUMENTS

| 7,720,692 | B2 | 5/2010 | Glimp et al. | |
| 7,761,309 | B2 | 7/2010 | Sacco et al. | |
| 8,019,582 | B2* | 9/2011 | Iliff | G16H 70/60 |
| | | | | 703/11 |
| 9,824,190 | B2* | 11/2017 | Sudharsan | G16H 50/50 |

(Continued)

FOREIGN PATENT DOCUMENTS

CN  108986907  11/2018

OTHER PUBLICATIONS

Teknomo, Kardi. "KNN Numerical Example (hand computation)". Revoledu (https://people.revoledu.com/kardi/). 2017. (Year: 2017).*

(Continued)

*Primary Examiner* — Robert A Sorey
*Assistant Examiner* — Kristine K Rapillo
(74) *Attorney, Agent, or Firm* — Caldwell Intellectual Property Law, LLC

(57) ABSTRACT

A system for prioritizing user symptom complaint inputs. The system includes a KNN module operating on at least a computing device configured to receive a plurality of symptom complaint datums, receive suspected disease state training data, calculate an optimal vector output utilizing a k-nearest neighbor algorithm and generate an optimal vector output containing a suspected disease state. The system includes a triage module operating on at least a computing device configured to receive the optimal vector output, generate a triage urgency category label, select triage training data as a function of the triage urgency label, generate using a supervised machine-learning model a disease criticality model, evaluate the disease criticality score, and display the ranked disease criticality score for each of the plurality of suspected disease states.

20 Claims, 10 Drawing Sheets

(56) References Cited

U.S. PATENT DOCUMENTS

| | | |
|---|---|---|
| 10,026,508 B2 | 7/2018 | Silva et al. |
| 2011/0054946 A1 | 3/2011 | Coulter et al. |
| 2012/0209625 A1* | 8/2012 | Armstrong ............. G16H 70/40 |
| | | 705/3 |
| 2014/0019162 A1 | 1/2014 | Skowronski et al. |
| 2017/0242973 A1* | 8/2017 | Levin ..................... G16H 50/20 |
| 2018/0130555 A1 | 5/2018 | Chronis et al. |
| 2018/0218127 A1* | 8/2018 | Salazar .................. G16H 50/30 |
| 2018/0239871 A1 | 8/2018 | Barkan et al. |
| 2018/0315488 A1 | 11/2018 | Miranda et al. |
| 2019/0057773 A1 | 2/2019 | Li |
| 2019/0180868 A1 | 6/2019 | Makram et al. |

OTHER PUBLICATIONS

Enriko et al., Heart Disease Diagnosis System With K-Nearest Neighbors Methos Using Real Clinical Medical Records; University of Indonesia; Jun. 2018.

* cited by examiner

METHODS AND SYSTEMS FOR PRIORITIZING USER SYMPTOM COMPLAINT INPUTS

FIELD OF THE INVENTION

The present invention generally relates to the field of artificial intelligence. In particular, the present invention is directed to methods and systems for prioritizing user symptom complaint inputs.

BACKGROUND

Accurate recommendations for prioritizing medical attention and treatment of user complaints is fraught with inaccuracies. Knowing what to treat first and when to seek treatment can be confusing. Inaccurate prioritization can lead to devastating results often causing complaints to go untreated and frustrating patients and medical professionals alike.

SUMMARY OF THE DISCLOSURE

In an aspect, A system for prioritizing user symptom complaint inputs. The system includes at least a computing device, wherein the at least a computing device further comprises one or more network interfaces; a non-volatile memory; and including one or more processors. The system includes a KNN module operating on the at least a computing device the KNN module designed and configured to receive a plurality of symptom complaint datums generated by a user at a graphical user interface operating on the at least a computing device; receive suspected disease state training data correlating at least an element of symptom complaint data to suspected disease states from an expert knowledge database located on the at least a computing device; calculate an optimal vector output for each of the plurality of symptom complaint datums utilizing a k-nearest neighbor algorithm and the suspected disease state training data; and generate an optimal vector output containing a suspected disease state for each of the plurality of symptom complaint datums. The system includes a triage module operating on the at least a computing device the triage module designed and configured to receive the optimal vector output containing a suspected disease state for each of the plurality of symptom complaint datums; generate a triage urgency category label for each of the plurality of suspected disease states wherein the triage urgency category label further comprises matching the optimal vector output containing a suspected disease state for each of the plurality of symptom complaint datums to a triage urgency category label; select triage training data as a function of the triage urgency category label for each of the plurality of suspected disease states wherein the triage training data correlates suspected disease states to relative disease criticality scores; generate using a supervised machine-learning model a disease criticality model that outputs a disease criticality score for each of the plurality of suspected disease states utilizing the selected triage training data; evaluate the disease criticality score for each of the plurality of suspected disease states as a function of ranking the disease criticality score for each of the plurality of suspected disease states; and display the ranked disease criticality score for each of the plurality of suspected disease states at the graphical user interface operating on the at least a computing device.

In an aspect, a method of prioritizing user symptom complaint inputs the system comprising receiving by at least a computing device a plurality of symptom complaint datums generated by a user at a graphical user interface operating on the at least a computing device; receiving by the at least a computing device a suspected disease state training data correlating at least an element of symptom complaint data to suspected disease states from an expert knowledge database located on the at least a computing device; calculating by the at least a computing device an optimal vector output for each of the plurality of symptom complaint datums utilizing a k-nearest neighbor algorithm and the suspected disease state training data; generating by the at least a computing device an optimal vector output containing a suspected disease state for each of the plurality of symptom complaint datums; generating by the at least a computing device a triage urgency category label for each of the plurality of suspected disease states wherein the triage urgency category label further comprises matching the optimal vector output containing a suspected disease state for each of the plurality of symptom complaint datums to a triage urgency category label; selecting by the at least a computing device a triage training data as a function of the triage urgency category label for each of the plurality of suspected disease states wherein the triage training data correlates suspected disease states to relative disease criticality scores; generating by the at least a computing device using a supervised machine-learning model a disease criticality model that outputs a disease criticality score for each of the plurality of suspected disease states utilizing the selected triage training data; evaluating by the at least a computing device the disease criticality score for each of the plurality of suspected disease states as a function of ranking the disease criticality score for each of the plurality of suspected disease states; and displaying by the at least a computing device the ranked disease criticality score for each of the plurality of suspected disease states at the graphical user interface operating on the at least a computing device.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for prioritizing user symptom complaint inputs. In an embodiment, at least a computing device receives a plurality of symptom complaint datums generated by a user at a graphical user interface. Plurality of symptom complaint datums may include descriptions of body symptoms that a user may be experiencing such as for example fatigue, left shoulder pain, weakness, and insomnia. At least a computing device receives suspected disease state training data correlating at least an element of symptom complaint data to suspected disease states from an expert knowledge database. At least a computing device calculates an optimal vector output for each of the plurality of symptom complaint datums using a k-nearest neighbor algorithm and the suspected disease state training data. At least a computing device generates a triage urgency category label for each of the plurality of suspected disease states. Triage urgency category label may contain an indication as to how soon medical attention may be needed. At least a computing device selects triage training data as a function of the triage urgency category label for each of the plurality of suspected disease states wherein the triage training data correlates suspected disease states to relative disease criticality scores. At least a computing device generates utilizing a supervised machine-learning model a disease criticality model that outputs a disease criticality score for each of the plurality of suspected disease states utilizing the selected triage training data. At least a computing device evaluates the disease criticality score for each of the plurality of suspected disease states as a function of ranking the disease criticality score. At least a computing device displays the ranked disease criticality score for each of the plurality of suspected disease states at the graphical user interface operating on at least a computing device.

Figure 1:
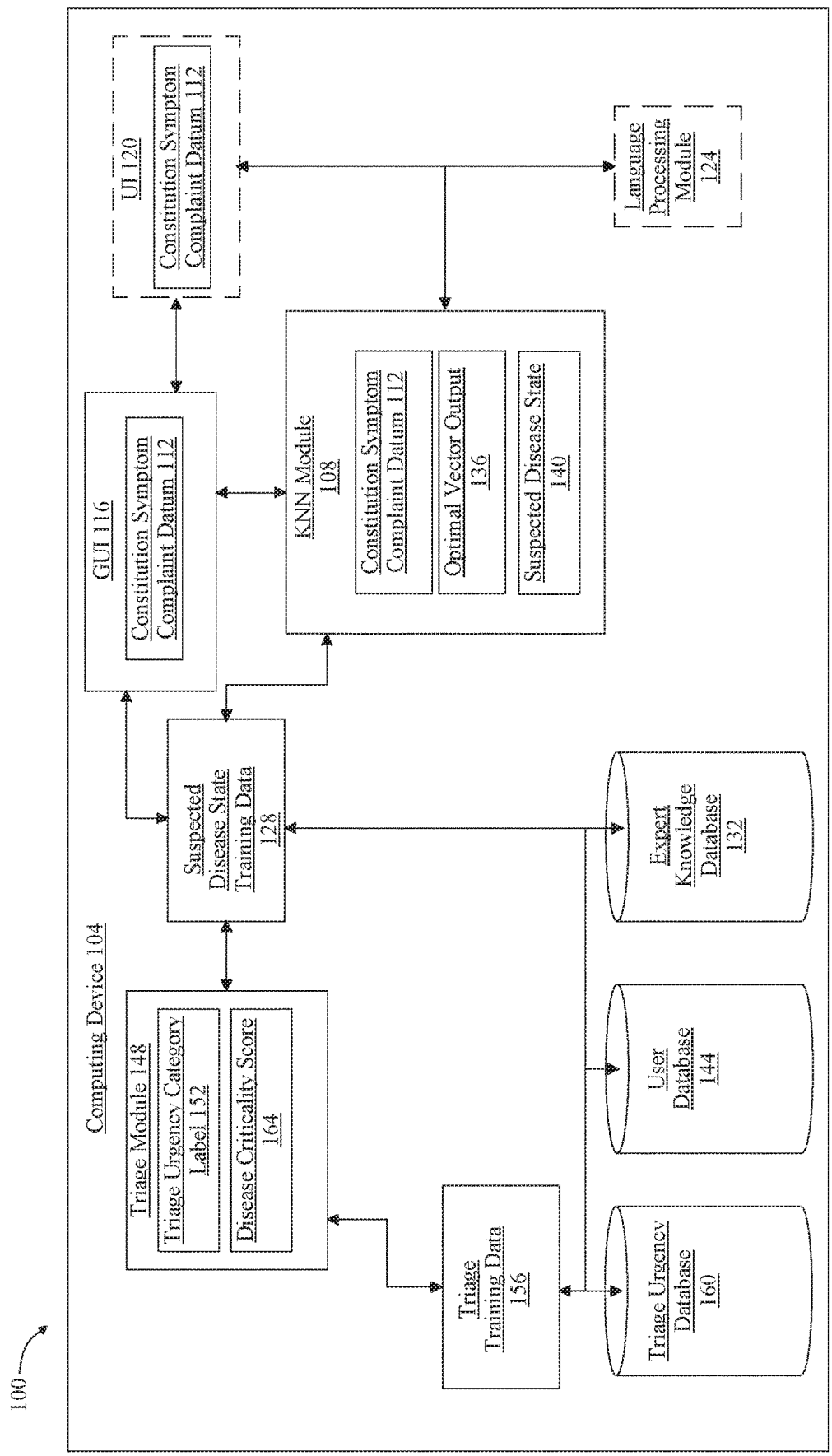
FIG. 1 is a block diagram illustrating an exemplary embodiment of a system for prioritizing user symptom complaint inputs.

Referring now to FIG. 1, an exemplary embodiment of a system 100 for prioritizing user symptom complaints is illustrated. System 100 includes at least a computing device 104, wherein the at least a computing device 104 further comprises one or more network interfaces, a non-volatile memory, and including one or more processors. Computing device 104, as used herein, includes any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include at least a server. At least a server may include a single computing device 104 operating independently, or may include two or more computing device 104 operating in concert, in parallel, sequentially or the like; two or more computing device 104 may be included together in a single computing device 104 or in two or more computing device 104. At least a server may interact with one or more additional devices as described below in further detail via a network interface device. Network interface device may be utilized for connecting at least a server to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing device 104, and any combinations thereof. A network may employ a wired and/or a wireless mode of communication. In general, any network topology may be used. Information (e.g., data, software etc.) may be communicated to and/or from a computer and/or a computing device 104. At least a server may include but is not limited to, for example, a computing device 104 or cluster of computing device 104 in a first location and a second computing device 104 or cluster of computing device 104 in a second location. At least a server may include one or more computing device 104 dedicated to data storage, security, distribution of traffic for load balancing, and the like. At least a server may distribute one or more computing tasks as described below across a plurality of computing device 104 of computing device 104, which may operate in parallel, in series, redundantly, or in any other manner used for distribution of tasks or memory between computing device 104. At least a server may be implemented using a "shared nothing" architecture in which data is cached at the worker, in an embodiment, this may enable scalability of system 100 and/or computing device 104.

With continued reference to FIG. 1, at least a computing device 104 may be designed and/or configured to perform any method, method step, or sequence of method steps in any embodiment described in this disclosure, in any order and with any degree of repetition. For instance, at least a computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. At least a computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, system 100 includes a k-nearest neighbors (KNN) module 108 operating on at least a computing device 104. KNN module 108 may include any hardware and/or software module. KNN module 108 is configured to receive a plurality of symptom complaint datums 112 generated by a user at a graphical user interface operating on at least a computing device 104. A "symptom complaint datum" as used in this disclosure, includes a description of any body symptom and/or medical condition that a user may be experiencing. A "body symptom" as used in this disclosure, includes any physical or mental feature which is regarded as indicating a condition and/or disease. Physical and/or mental feature may include any sign and/or symptom relevant to a potential medical condition and/or symptom. Physical and/or mental feature may include a sign such as clubbing on fingernails or a symptom such as mental fatigue. Body symptom may include dizziness, fever, tiredness, sleepiness, nausea, shortness of breath, abdominal pain, hearing loss, inability to pass urine, profusive sweating, alopecia, and the like. Body symptom may be located to one particular location of the body such as a body symptom that includes a description of pelvis pain or blurry vision in a user's left eye. Body symptom may be limited to one or more body systems such as a cardiovascular arrhythmia or abdominal bloating and fecal incontinence. Body symptom may be apparent as indicating to a user a particular condition and/or disease such as when a patient experiences a body symptom such as blood loss from a flesh wound. Body symptom may not be apparent as indicating to a user a particular condition and/or disease such as when a patient experiences a body symptom such as tiredness due to a thyroid condition which the user believes is simply due to being overly fatigued. Body symptom may include a remitting symptom, such as when symptoms improve or resolve completely. For instance and without limitation, symptoms of a common cold such as stuffy nose, headache, sneezing, and congested sinuses may occur for several days and then resolve with or without treatment. Body symptom may include a chronic symptom, such as when symptoms are long-lasting and recurrent. For example, foot pain experienced as a result of diabetic neuropathy may be long-lasting symptoms experienced throughout the duration of a user having diabetes. Body symptom may include a relapsing symptom, which may include a symptom that occurred in the past at some other point in time, resolved, and then returned. For example, symptoms of depression may not occur for years at a time but then may return without notice. Symptom complaint datum 112, may include a description of a body symptom that a user may be currently experiencing and/or recently experienced. For example, symptom complaint datum 112 may include a description of a blood coming out of a nostril or low back pain after sitting or a description of jaw pain that occurs upon waking.

With continued reference to FIG. 1, KNN module 108 receives a plurality of symptom complaint datums 112 generated by a user at a graphical user interface 116 operating on at least a computing device 104. Graphical user interface 116 may include without limitation, a form or other graphical element having data entry fields, wherein user may enter a plurality of symptom complaint datum 112. Graphical user interface 116 may include data entry fields that allow for a user to enter free form textual inputs describing a plurality of symptom complaint datum 112. Graphical user interface 116 may provide drop-down lists, where users may be able to select one or more entries to indicate one or more symptom complaint datum 112.

With continued reference to FIG. 1, KNN module 108 is further configured to receive a plurality of symptom complaint datum 112 generated by a user at a user interface 120 operating on at least a computing device 104. User interface 120 may perform, without limitation, speech-to-text algorithms that change oral inputs into text, which may allow for a user to enter oral spoken symptom complaint datum to textual symptom complaint datum. User interface 120 may utilize speech-to-text algorithms that include automatic speech recognition, computer speech recognition, and/or speech to text. User interface 120 may require training of user interface 120 whereby an individual may read text or vocabulary into the user interface 120 to train the system. In an embodiment, user interface 120 may recognize the voice of the user as they speak. User interface 120 may utilize models including Hidden Markov models, dynamic time warping based speech recognition, neural networks, deep feedforward and recurrent neural networks, and/or end-to-end automatic speech recognition.

With continued reference to FIG. 1, computing device 104 may include language processing module 124. Language processing module 124 may include any hardware and/or software module. Language processing module 124 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, language processing module 124 may operate to produce a language processing model. Language processing model may include a program automatically generated by at least a server and/or language processing module 124 to produce associations between one or more words extracted from at least a document and detect associations, including without limitation mathematical associations, between such words, and/or associations of extracted words. Associations between language elements, where language elements include for purposes herein extracted words, categories of physiological data, relationships of such categories to constitution symptom complaints may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of body symptoms. As a further example, statistical correlations and/or mathematical associations may include probabilistic formulas or relationships indicating a positive and/or negative association between at least an extracted word and/or a given category of symptoms; positive or negative indication may include an indication that a given document is or is not indicating a particular body symptom or is not significant. For instance, and without limitation, a negative indication may be determined from a phrase such as "head pain was not associated with neck pain," whereas a positive indication may be determined from a phrase such as "back pain was associated with decreased urine output," as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory on a computing device 104 or the like.

Still referring to FIG. 1, language processing module 124 and/or at least a computing device 104 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein, are statistical models with inference algorithms that that may be applied to the models. In such models, a hidden state to be estimated may include an association between an extracted word and a given relationship of an extracted word to a particular symptom. There may be a finite number of category of symptoms, and/or a given relationship of such words to category of symptoms; an HMM inference algorithm, such as the forward-backward algorithm or the Viterbi algorithm, may be used to estimate the most likely discrete state given a word or sequence of words. Language processing module 124 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module 124 may use a corpus of documents to generate associations between language elements in a language processing module 124, and at least a server may then use such associations to analyze words extracted from one or more documents and determine that the one or more documents indicate significance of a symptom. In an embodiment, at least a server may perform this analysis using a selected set of significant documents, such as documents identified by one or more experts as representing good science, good clinical analysis, or the like; experts may identify or enter such documents via graphical user interface 116 as described \, or may communicate identities of significant documents according to any other suitable method of electronic communication, or by providing such identity to other persons who may enter such identifications into at least a server. Documents may be entered into at least a server by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, at least a server may automatically obtain the document using such an identifier, for instance by submitting a request to a database or compendium of documents such as JSTOR as provided by Ithaka Harbors, Inc. of New York.

With continued reference to FIG. 1, KNN module 108 is configured to receive suspected disease state training data 128 correlating at least an element of symptom complaint data to suspected disease state vectors from an expert knowledge database located on at least a computing device 104. "Training data," as used in this disclosure, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by at least a server 104 may correlate any input data as described in this disclosure to any output data as described in this disclosure.

With continued reference to FIG. 1, KNN module 108 receives training data correlating at least an element of symptom complaint data to suspected disease state vectors. "Correlation" in a training data set may include any relation established therein linking one datum to another, including inclusion together in a data element, row, column, cell, or the like, and/or by giving each a common indicator and/or label indicative of their correlation in data used to create and/or compile training data. Correlation may include a relation established whereby at least an element of symptom complaint data is correlated to suspected disease state 140 vector based on data entries obtained from the same subject. Training set may include a plurality of entries, each entry correlating at least an element of symptom complaint data to suspected disease state vectors.

With continued reference to FIG. 1, suspected disease state 140 vector may be a data structure that represents a quantitative measure of a degree of probability of a user receiving a diagnosis from a medical professional for having a particular disease and/or condition. Medical professional may include any licensed health professional who may be authorized by a medical licensing board to diagnose disease and/or conditions including for example, a medical doctor, a doctor of osteopathy, a nurse practitioner, a physician assistant, a doctor of optometry, a doctor of dental medicine, a doctor of dental surgery, a naturopathic doctor, a doctor of physical therapy, a nurse, a doctor of chiropractic medicine, a doctor of oriental medicine, and the like. A "suspected disease state 140 vector" as defined in this disclosure, is n n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\Sigma_{i=0}^{n} a_i^2}$, where a is attribute number i of the vector. Scaling and/or normalization may function to make vector comparison independent of absolute quantities of attributes, while preserving any dependency on similarity of attributes; this may, for instance be advantageous where each vector represents a weighing of user priorities, and/or is to be compared to such a weighing of user priorities.

With continued reference to FIG. 1, KNN module 108 receives suspected disease state training data 128 from an expert knowledge database 132 located on at least a computing device 104. Expert knowledge database 132 may include any data structure for ordered storage and retrieval of data, which may be implemented as a hardware or software module. An expert knowledge database 132 may be implemented, without limitation, as a relational database, a key-value retrieval datastore such as a NOSQL database, or any other format or structure for use as a datastore that a person skilled in the art would recognize as suitable upon review of the entirety of this disclosure. Expert submissions may be provided in any suitable manner, including using on or more entries on a graphical user interface 116, for instance according to embodiments as described in further detail below.

With continued reference to FIG. 1, KNN module 108 is configured to calculate an optimal vector output 136 for each of the plurality of symptom complaint datum 112 utilizing a k-nearest neighbor algorithm and suspected disease state training data 128. "Optimal vector output 136" as used in this disclosure, includes a "first guess" by KNN module 108 at the nearest vector in the feature space containing a suspected disease state 140. K-nearest neighbor algorithm may return a single matching entry or a plurality of matching entries. When a plurality of matching entries are returned, KNN module 108 may derive optimal vector from plurality of matching entries by aggregating matching entries; aggregation may be performed using any suitable method for aggregation, including component-wise addition followed by normalization, component-wise calculation of arithmetic means, or the like. "K-nearest neighbor algorithm" as used in this disclosure, includes a lazy-learning method that utilizes feature similarity to analyze how closely out-of-sample-features resemble training data to locate possible optimal vector output 136, classify possible optimal vector output 136, calculate an optimal vector output 136, and generate an optimal vector output 136. Calculating an optimal vector output 136 utilizing a k-nearest neighbor algorithm may include specifying a K-value, selecting k entries in a database which are closest to the known sample, determining the most common classifier of the entries in the database, and classifying the known sample. A lazy-learning process and/or protocol, which may alternatively be referred to as a "lazy loading" or "call-when-needed" process and/or protocol, may be a process whereby machine-learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data. Heuristic may include selecting some number of highest-ranking associations and/or training data elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

With continued reference to FIG. 1, KNN module 108 is configured to calculate an optimal vector output 136 by identifying the presence of a symptom complaint datum 112 and confirming a suspected disease state. "Confirming a suspected disease state" as used in this disclosure, includes identifying a suspected disease state that may be included in optimal vector output 136. Suspected disease state 140 may include a disease state and/or condition that may be subsequently diagnosed by a medical professional due to the presence or absence of symptoms experienced by a user. Medical professional may include any of the medical professionals as described herein. Suspected disease state 140 may include a probable current disease state and/or medical condition and/or future probable disease state and/or medical condition. For instance and without limitation, presence of a symptom such as a resting tremor may confirm a possible suspected disease state 140 such as Parkinson's disease. In yet another non-limiting example, presence of a symptom such as head pain may be utilized to confirm a possible suspected disease state 140 such as migraine. In an embodiment, presence of a symptom may be utilized to confirm a plurality of suspected disease state 140. For instance and without limitation, a symptom such as knee pain may be utilized to confirm a plurality of suspected disease state 140 that include osteoarthritis, Lyme disease, and jumper's knee. In yet another non-limiting example, a symptom such as fatigue may be utilized to confirm a plurality of suspected disease state 140 that include anemia, chronic fatigue syndrome, hypothyroidism, and fibromyalgia. Identification of the presence of a symptom complaint datum 112 may be utilized to eliminate a suspected disease state 140. For instance and without limitation, presence of a symptom such as left toe pain may be utilized to eliminate a suspected disease state 140 such as myocardial infarction. In yet another non-limiting example, presence of a symptom such as tinnitus may be utilized to eliminate a suspected disease state 140 such as acid reflux disease. Identification of the presence of a symptom complaint datum 112 may be utilized to eliminate a plurality of suspected disease state 140. For instance and without limitation, presence of a symptom such as a productive wet cough may be utilized to eliminate a plurality of suspected disease state 140 such as anxiety, dementia, and urinary tract infection.

With continued reference to FIG. 1, absence of a symptom may be utilized to confirm a possible suspected disease state 140. For instance and without limitation, absence of a symptom such as absence of fever may be utilized to confirm a possible suspected disease state 140 such as parvovirus. Absence of a symptom may be utilized to eliminate a possible suspected disease state 140. For instance and without limitation, absence of a symptom such as diarrhea may be utilized to eliminate a possible suspected disease state 140 such as ulcerative colitis. In yet another non-limiting example, absence of a symptom such as sweaty palms may be utilized to eliminate a possible suspected disease state 140 such as hyperhidrosis.

With continued reference to FIG. 1, KNN module 108 is configured to generate an optimal vector output 136 containing a suspected disease state 140 for each of the plurality of symptom complaint datums 112. Optimal vector output 136 includes any of the optimal vector output 136 as described herein. Suspected disease state 140 includes any of the suspected disease state 140 as described herein.

With continued reference to FIG. 1, generating an optimal vector output 136 includes displaying the optimal vector output 136 containing a suspected disease state 140 to a user, receiving a user entry containing a datum of user genetic history, and updating the optimal vector output 136 containing a new suspected disease state 140 as a function of the user entry. An optimal vector output 136 may be displayed to a user via computing device 104, such as for example by displaying optimal vector output 136 on a graphical user interface 116 indicating a first guess at a suspected disease state 140. Graphical user interface 116 may include any of the graphical user interfaces 116 as described above. In an embodiment, optimal vector output 136 may display a plurality of suspected disease state 140. User entry generated in response to displaying an optimal vector output 136 contains a datum of user genetic history. "User genetic history" as used in this disclosure, includes a sample extracted from a user that includes any sequence of nucleic acid identified in a user, including without limitation deoxyribonucleic acid (DNA) and/or ribonucleic acid (RNA). DNA may include chromosomal DNA, including without limitation sequences encoding particular genes as well as sequences of DNA disposed between or after gene sequences, including without limitation telomeres. Telomeres, as used in this description are caps (repetitive nucleotide sequences) at the end of linear chromosomes of a user. Telomeres are theorized to play a critical role in facilitating complete chromosome replication. Telomeres are characterized by noncoding tandem arrays of a "TTAGGG" DNA sequence that are located at the terminal ends of all vertebrate chromosomes, including those of humans. A G-rich single stranded 3-prime overhang is present at the end of human telomeres; this overhang, which may be important for telomere function folds back on itself forming a large loop structure called a telomere loop, or T-loop, that has a shape similar to that of a paper clip. A telomere may be stabilized by a six-protein complex, known as "shelterin," which may include telomeric repeat binding factor 1 and 2 (TRF1 and TRF2), protection of telomeres 1 (POT1), TRF1 and TRF2 interacting nuclear protein 2 (TIN2), the human ortholog of the yeast repressor/activator protein 1 (Rap1), and TPP1. Telomere lengths have been observed to reduce over a series of cellular mitotic divisions, such that telomere length and/or changes in telomere length appear to correlate with processes of cellular aging and senescence. It is therefore hypothesized that telomere length and/or changes thereto may be useful to predict life expectancy of a person; however, precise predictions have hitherto eluded researchers. A genetic sample may include mRNA, tRNA, or any other RNA sequence or strand.

With continued reference to FIG. 1, user genetic history may be obtained from a physically extracted sample. "Physically extracted sample" as used in this disclosure, includes any methodology, equipment, device, and/or instrument utilized to collect a genetic history from a user. Physically extracted sample may include for example a tissue sample, a buccal swab, a fluid sample, a biopsy, a blood sample, a hair sample, a sample obtained from a microchip sensor placed under the skin, and the like. Physically extracted sample may be further processed such as by polymerase chain reaction "PCR" processes, centrifuge processes, subsequences, and the like.

With continued reference to FIG. 1, KNN module 108 may receive a user entry containing a datum of user genetic history from a user database 144 operating on at least a computing device 104. User database 144 may be implemented in any way suitable for implementation of expert database as described above. User database 144 may include a plurality of data entries and/or records corresponding to user genetic history. Data entries in user database 144 may include additional elements of information such as user demographic information which may be reflected in data entry cells and/or in linked tables such as tables related by one or more indices in a relational database. Persons skilled in the art, upon reviewing the entirety of this disclosure, will be aware of various ways in which data entries in a user database 144 may be organized.

With continued reference to FIG. 1, optimal vector output 136 may be updated to contain a new suspected disease state 140 as a function of user entry. Optimal vector output 136 may be updated to select and/or eliminate suspected disease state 140 as a function of user entry containing a datum of user genetic history. For instance and without limitation, a datum of user genetic history showing one copy of inherited HbSS gene may be utilized to select a suspected disease state 140 that includes sickle cell disease. In yet another non-limiting example, a datum of user genetic history showing an A/G genotype matrix for the MCMG gene that controls production of lactase may be utilized to select a suspected disease state 140 that includes lactose intolerance. In yet another non-limiting example, a datum of user genetic history showing an A/A genotype matrix for the MCMG gene that controls production of lactase may be utilized to eliminate a suspected disease state 140 that includes lactose intolerance. In yet another non-limiting example, a datum of user genetic history showing Greek ancestry may be utilized to select a suspected disease state 140 that includes thalassemia. In yet another non-limiting example, a datum of user genetic history showing ancestry that is not of sub-Saharan African ancestry may be utilized to eliminate a suspected disease state 140 that includes sickle-cell anemia.

With continued reference to FIG. 1, system 100 includes a triage module 148 operating on at least a computing device 104. Triage module 148 includes any hardware and/or software module. Triage module 148 is configured to receive at optimal vector output 136 containing a suspected disease state 140 for each of the plurality of symptom complaint datum 112.

With continued reference to FIG. 1, triage module 148 is configured to generate a triage urgency category label 152 for each of the plurality of constitution complaint datums wherein the triage urgency category label 152 further comprises matching an optimal vector output 136 containing a suspected disease state 140 for each of the plurality of symptom complaint datum 112 to a triage urgency category label 152. "Triage urgency category label 152" as used in this disclosure, includes a datum describing how urgent a particular suspected disease state 140 for each of the plurality of symptom complaint datum 112 warrants medical attention. "Medical attention" as used in this disclosure, includes treatment received from a medical professional. Treatment may include actual face to face treatment with a medical professional and/or virtual treatment such as through an electronic video chat, web-chat, and/or phone call with a medical professional. Medical professional may include any of the medical professionals as described herein. Triage urgency category label 152 may include an immediate attention label when medical attention is needed within the next hour. Triage urgency category label 152 may include an attention in the near future label when medical attention is needed within the next three hours. Triage urgency category label 152 may include an attention in the next day label when medical attention is needed within the next twenty four hours. Triage urgency category label 152 may include an attention in the next week label when medical attention is needed within one week. Triage urgency category label 152 may include a check-up appointment label when medical attention can be delayed until a subsequently scheduled appointment. Triage urgency category label 152 may include a self-care label when medical attention is not warranted, and a user can utilize home treatment such as when utilizing over the counter and non-prescription treatments.

With continued reference to FIG. 1, triage module 148 may match an optimal vector output 136 containing a suspected disease state 140 to a triage urgency category label 152. Matching may include calculating a triage urgency algorithm that may be indicative in determining how soon medical attention is needed. Triage urgency algorithm includes multiplying a body system factor by a life endangerment factor and an alarm condition factor. Triage urgency algorithm may output a numerical score with each factor utilized to calculate triage urgency algorithm being given an individual score that is multiplied together. Higher final values for triage urgency algorithm may indicate a need for more immediate medical attention. Expert input provided for example through expert database may provide input for values of different factors assigned to different suspected disease state 140 and/or symptom complaints. Expert input provided for example through expert database may provide start and end ranges for final triage urgency algorithm scores that may be categorized as belonging to a particular triage urgency category label 152. For instance and without limitation, a particular range of scores between a start score and an end score may be indicative of a triage urgency category label 152 such as check-up appointment label while another particular range of scores between a start score and an end score may be indicative of a triage urgency category label 152 such as immediate attention label. "Body system factor" as used in this disclosure, is a factor that may indicate a particular body system that is involved with a particular suspected disease state 140 and/or symptom complaint. Expert input may provide guidance as to which suspected disease state 140 and/or symptom complaints affecting particular body systems may warrant particular levels of medical attention. For instance and without limitation, a particular suspected disease state 140 such as irritable bowel syndrome that affects the gastrointestinal tract may contain a lower body system factor that does not need immediate medical attention, while a suspected disease state 140 such as a suspected heart attack affecting the cardiovascular system may contain a higher body system factor that does need immediate medical attention. In yet another non-limiting example, a suspected disease state 140 such as a cut on one's toe that affects the integumentary system may contain a lower body system factor that can be treated at home, while a suspected disease state 140 such as a concussion that affects the neurological system may contain a higher body system factor that does need immediate medical attention. "Life endangerment factor" as used in this disclosure, is a factor that may indicate a particular life threatening condition. Expert input may provide guidance as to which suspected disease state 140 and/or symptom complaints may be life threatening and may require more immediate medical attention. For instance and without limitation, a particular suspected disease state 140 such as Raynaud's syndrome may contain a lower score indicating a non-urgent need for medical attention while a particular suspected disease state 140 such as a hypertensive crisis may contain a higher score indicating an urgent need for medical attention. In yet another non-limiting example, a particular suspected disease state 140 such as toenail fungus may contain a very low score indicating an ability to self-treat at home, while a particular suspected disease state 140 such as rectal bleeding may contain a higher score indicating a more urgent need for medical attention. "Alarm condition factor" as used in this disclosure, is a factor that may indicate how necessary immediate medical attention for a particular suspected disease state 140 and/or symptom complaint may be needed. Expert input may provide guidance as to how urgent treatment for a particular suspected disease state 140 and/or symptom complaint may be needed. For instance and without limitation, a particular suspected disease state 140 such as chest pain may contain an alarm condition factor score indicating a more urgent need for treatment while a particular suspected disease state 140 such as a backache may contain a lower alarm condition factor treatment indicating a less urgent need for treatment. In yet another non-limiting example, a particular suspected disease state 140 such as loss of consciousness may contain a higher alarm condition factor score indicating a more urgent need for treatment while a particular suspected disease state 140 such as a skin rash may contain a lower alarm condition factor score indicating a less urgent need for treatment.

With continued reference to FIG. 1, triage module 148 is configured to select triage training data 156 as a function of the triage urgency category label 152 for each of the plurality of suspected disease state 140 wherein the triage training data 156 correlates suspected disease state 140 to relative disease criticality scores. "Disease criticality score" as used in this disclosure, indicates how critical medical attention and/or treatment may be needed for a particular disease. Triage training set may include a plurality of entries, each entry correlating at least a suspected disease state 140 to a relative disease criticality score. For instance and without limitation, triage training set may include a data entry that includes a suspected disease state 140 such as measles having a high disease criticality index score indicating the need for immediate treatment. In yet another non-limiting example, triage training set may include a data entry that includes a suspected disease state 140 such as tooth ache having a low disease criticality index score indicating less of a need for immediate medical treatment. Disease criticality score may be further subdivided to include an intervention score, a constitutional expert score, and an alternative treatment score. "Intervention score" as used in this disclosure, indicates how soon medical intervention may be needed as a function of a suspected disease state 140. Medical intervention includes medical procedure and/or course of action that may help in treating disease, medical conditions, and/or injury. Medical intervention may include medical procedures that include outpatient procedures such as an x-ray, magnetic resonance image (MM), biopsy, screening test such as a colonoscopy or endoscopy, dental restoration, arthroscopy, burn debridement, platelet-rich plasma (PRP) injection, and the like. Medical intervention may include medical procedures that include inpatient procedures such as angiocardiography, cesarean section, diagnostic ultrasound, cardiac catheterization, knee replacement, insertion of coronary artery stent, hip replacement and the like. For example, a suspected disease state 140 such as coronary artery disease may have a higher intervention score indicating that medical intervention necessary to reverse and/or treat coronary artery disease is needed sooner as compared to a suspected disease state 140 such as an ingrown toenail which may have a lower intervention score indicating that medical intervention is not needed as quickly. "Constitutional expert score" as used in this disclosure, indicates how soon an appointment with a medical professional should occur as a function of a suspected disease state 140. For example, a suspected disease state 140 such as Lupus may warrant a higher constitutional expert score indicating an appointment with a medical professional in the very near immediate future is necessary as compared to a suspected disease state 140 such as fatigue which may warrant a lower constitutional expert score indicating an appointment with a medical professional does not have to occur immediately but may be suitable at a follow up appointment later on. "Alternative treatment score" as used in this disclosure, indicates how likely a particular suspected disease state 140 can be managed with alternative treatments. Alternative treatments may include over the counter medications such as nutraceuticals, homeopathic remedies, vitamins, minerals, supplements, natural remedies, herbals, and the like. For instance and without limitation, a suspected disease state 140 such as adrenal fatigue may contain a high alternative treatment score indicating a high likelihood of being managed with alternative treatments while a suspected disease state 140 such as acute myocardial infarction may contain a low alternative treatment score indicating a low likelihood of being managed with alternative treatments.

With continued reference to FIG. 1, triage module 148 is configured to select triage training data 156. Triage module 148 may select triage training data 156 by matching a suspected disease state 140 to triage training data 156 containing the suspected disease state 140 contained within a triage urgency category label 152 database. Triage urgency category label 152 database may be implemented in any way suitable for implementation of expert database as described above. Triage urgency category label 152 database may include a plurality of data entries and/or records corresponding to particular triage training sets. Triage training sets may be organized according to triage urgency category label 152 ad described in more detail below. Data entries in triage urgency category label 152 database may include additional elements of information which may be reflected in data entry cells and/or in linked tables such as tables related by one or more indices in a relational database. In an embodiment, triage module 148 may select triage training data 156 by first matching triage urgency category label 152 to the same triage urgency category label 152 contained within triage urgency category label 152 database and then to a triage training set containing a suspected disease state 140 contained within the match triage urgency category label 152. Selecting triage training data 156 as a function of the triage urgency category label 152 includes selecting a first triage training set from a triage urgency category label 152 database as a function of the triage urgency category label 152, probing the first triage training set to locate a suspected disease state 140 and failing to locate the suspected disease state 140 within the first triage training set, discarding the first training set, selecting a second triage training set from the triage urgency category label 152 database as a function of the triage urgency category label 152, probing the second triage training set to locate a suspected disease state 140 and locating the suspected disease state 140 within the second triage training set, and selecting the second triage training set. Selecting triage training data may include choosing a supervised machine-learning disease criticality model that was already created using a particular triage training data set that is stored on at least a computing device 104 and precomputed which can be utilized to generate outputs when given any particular inputs. In an embodiment, at least a computing device 104 may include a database containing precomputed disease criticality models that may be selected. Persons skilled in the art, upon reviewing the entirety of this disclosure, will be aware of various ways in which data entries in triage urgency category label 152 database may be organized.

With continued reference to FIG. 1, triage module 148 is configured to generate using a supervised machine-learning processes a disease criticality model that receives each of the plurality of suspected disease state 140 and outputs a disease criticality score 164 for each of the plurality of suspected disease state 140 utilizing the selected training data. Supervised machine-learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include suspected disease state 140 produced via lazy-learning processes as described above, disease criticality scores 164 as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine-learning algorithms that may be used to determine relation between inputs and outputs.

With continued reference to FIG. 1, triage module 148 is configured to generate using a supervised machine-learning processes a disease criticality model that outputs a disease criticality score 164 for each of the plurality of suspected disease state 140 utilizing the selected triage training data 156. Supervised machine-learning processes may include classification algorithms, defined as processes whereby a computing device 104 derives, from training data, a model for sorting inputs into categories or bins of data. Classification may be performed using, without limitation, linear classifiers such as without limitation logistic regression and/or naive Bayes classifiers, nearest neighbor classifiers, support vector machines, decision trees, boosted trees, random forest classifiers, and/or neural network-based classifiers.

Still referring to FIG. 1, machine-learning processes as described in this disclosure may be used to generate machine-learning models. A machine-learning model, as used herein, is a mathematical representation of a relationship between inputs and outputs, as generated using any machine-learning process including without limitation any process as described above, and stored in memory; an input is submitted to a machine-learning model once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model may be generated by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning, for instance for multi-layered networks.

With continued reference to FIG. 1, triage module 148 is configured to evaluate the ranked disease criticality score for each of the plurality of suspected disease state 140 as a function of ranking the disease criticality score 164 for each of the plurality of suspected disease state 140. Ranking may include classifying suspected disease state 140 as a function of disease criticality score 164. Ranking may include classifying suspected disease state 140 such as in descending order of disease criticality score 164 whereby a suspected disease state 140 with the highest disease criticality score 164 may be ranked first and a suspected disease state 140 with the lowest disease criticality score 164 may be ranked last. In an embodiment, ranking may include ranking suspected disease state 140 into sub-classifiers whereby suspected disease state 140 that affect a particular body system such as the nervous system may be ranked into a hierarchy of suspected disease state 140 with the highest disease criticality score 164 ranked first that affects the nervous system and a suspected disease state 140 with the lowest disease criticality score 164 that affects the nervous system may be ranked last.

With continued reference to FIG. 1, evaluating the ranked disease criticality score for each of the plurality of suspected disease state 140 includes receiving at least a user input datum wherein the at least a user input datum further comprises a previous user diagnosis, selecting a suspected disease state 140 as a function of the previous user diagnosis and the ranked disease criticality score and displaying the selected suspected disease state 140 at a graphical user interface 116 operating on at least a computing device 104. Previous user diagnosis may include a description of a previous medical condition and/or disease state that a user may have received from a medical professional. Previous user diagnosis may be utilized to select and/or eliminate particular suspected disease state 140. For instance and without limitation, a previous user diagnosis such as Celiac Disease may be utilized to eliminate a suspected disease state 140 from a plurality of suspected disease such as gluten intolerance because the user is already on a gluten free diet having received a previous diagnosis of Celiac Disease. In yet another non-limiting example, a previous user diagnosis such as Celiac Disease may be utilized to select a suspected disease state 140 such as lactose intolerance because of a known link between Celiac Disease and lactose intolerance.

With continued reference to FIG. 1, triage module 148 is configured to display the ranked disease criticality score for each of the plurality of suspected disease state 140 at a graphical user interface 116 operating on at least a computing device 104. Displaying the ranked disease criticality score may include displaying any sub-groups that may be ranked as described in more detail above.

Figure 2:
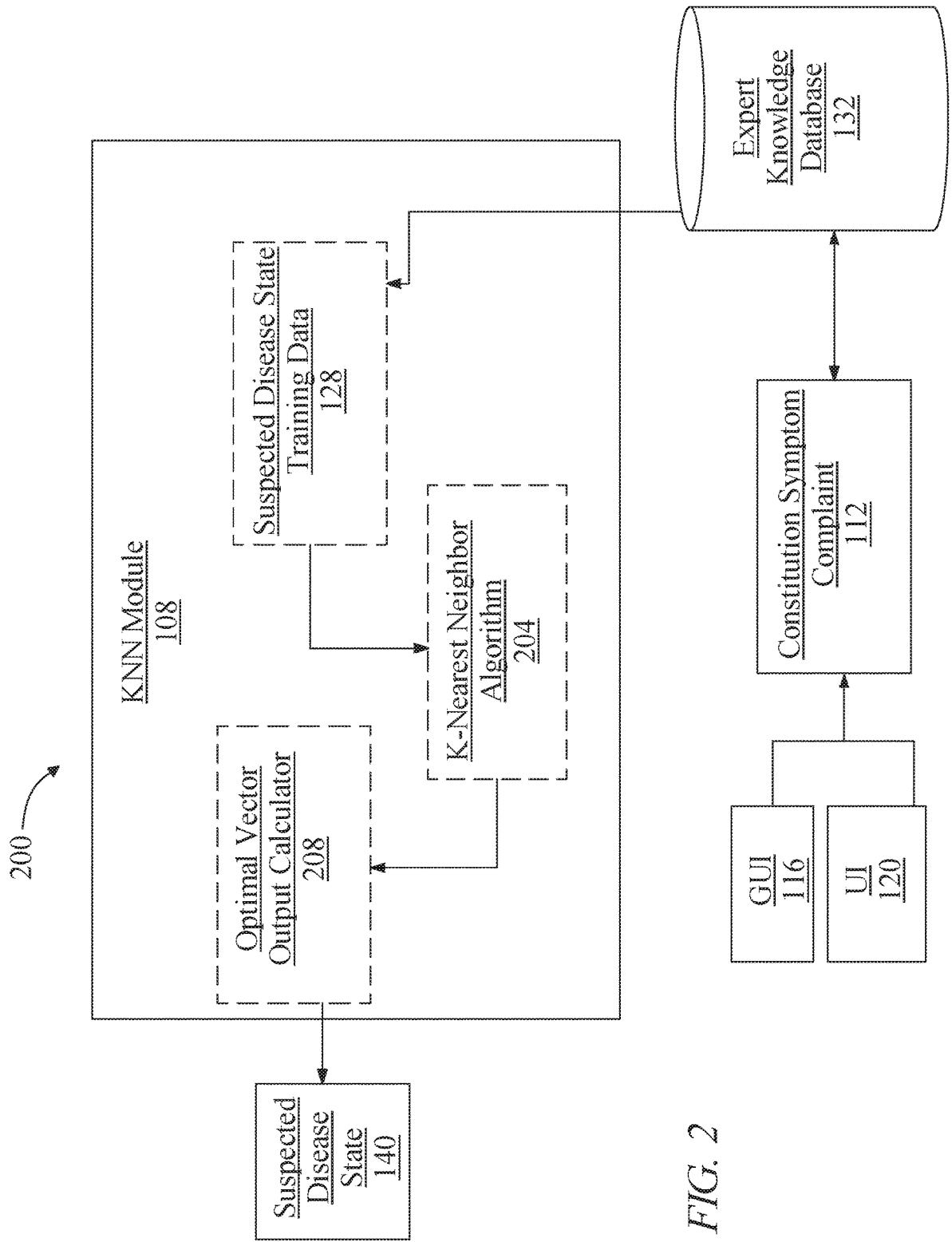
FIG. 2 is a block diagram illustrating an exemplary embodiment of a KNN module.

Referring now to FIG. 2, an exemplary embodiment 200 of KNN module 108 is illustrated. KNN module 108 may be implemented as a hardware or software module. KNN module 108 is configured to receive a plurality of symptom complaint datum 112 generated by a user at a graphical user interface 116 operating on at least a computing device 104, receive suspected disease state training data 128 correlating at least an element of symptom complaint data to suspected disease state vectors from an expert knowledge database 132 located on the at least a computing device 104, calculate an optimal vector output 136 for each of the plurality of symptom complaint datum 112 utilizing a k-nearest neighbor algorithm 204 and the suspected disease state training data 128, and generate an optimal vector output 136 containing a suspected disease state 140 for each of the plurality of symptom complaints.

With continued reference to FIG. 2, KNN module 108 receives a plurality of symptom complaint datum 112 generated by a user at a graphical user interface 116 and/or user interface 120 as described above in more detail in reference to FIG. 1. Plurality of symptom complaint datum 112 may contain a description of body symptoms and/or medical conditions that a user may be experiencing. For instance and without limitation, plurality of symptom complaint datum 112 may include a first symptom complaint datum 112 that includes a symptom such as "head pain," a second symptom complaint datum 112 that includes a symptom such as "watery eyes," and a third symptom complaint datum 112 that includes a symptom such as "wet productive cough." In an embodiment, user may enter plurality of symptom complaint datum 112 through user interface 120 featuring a spoken option wherein the user interface 120 converts oral spoken symptom complaint datum 112 to textual symptom complaint datum 112.

With continued reference to FIG. 2, KNN module 108 receives suspected disease state training data 128 correlating at least an element of symptom complaint data to suspected disease state 140 from an expert knowledge database 132 located on at least a computing device 104. In an embodiment, expert knowledge database 132 may contain suspected disease state training data 128 organized by symptom complaints, whereby a symptom complaint datum is utilized to select a suspected disease state 140 training set located within expert knowledge database 132 as described in more detail below. Training data sets contained within expert knowledge database 132 may be received from expert inputs such as by top medical experts, journal articles, and scientific studies as described in more detail below.

With continued reference to FIG. 2, KNN module 108 may include an optimal vector output 136 calculator 208 that calculates an optimal vector output 136 for each of the plurality of symptom complaint datum 112 utilizing a k-nearest neighbor algorithm 204 and the suspected disease state training data 128. K-nearest neighbor algorithm 204 includes a lazy-learning process as described above in more detail in reference to FIG. 1. K-nearest neighbor algorithm 204 may generate a suspected disease state 140 output by classifying suspected disease state training data 128 to find the most similar data entries contained within the suspected disease state training data 128. KNN module 108 may modify suspected disease state training data 128 by representing suspected disease state training data 128 as vectors. Vectors may include mathematical representations of suspected disease state training data 128. Vectors may include n-tuple of values which may represent a measurement or other quantitative value associated with a given category of data, or attribute. Vectors may be represented in n-dimensional space using an axis per category of value represented in n-tuple of values, such that a vector has a geometric direction characterizing the relative quantities of attributes in the n-tuple as compared to each other. In an embodiment, KNN module 108 may calculate an initial heuristic ranking association between inputs and elements of suspected disease state training data 128. Initial heuristic may include selecting some number of highest-ranking associations and/or training data elements. KNN module 108 may perform one or more processes to modify and/or format suspected disease state training data 128. Suspected disease state training data 128 may contain "N" unique features, whereby a dataset contained within suspected disease state training data 128 and represented as a vector may contain a vector of length "N" whereby entry "I" of the vector represents that data point's value for feature "I." Each vector may be mathematically represented as a point in "$R^N$." For instance and without limitation, KNN module 108 may modify entries contained within suspected disease state training data 128 to contain consistent forms of a variance. After appropriate selection of suspected disease state training data 128 from expert knowledge database 132, KNN module 108 performs K-nearest neighbor algorithm 204 by classifying datasets contained within suspected disease state 140 training set. Suspected disease state training data 128 may be represented as an "M×N" matrix where "M" is the number of data points contained within the suspected disease state training data 128 and "N" is the number of features contained within the suspected disease state training data 128. Classifying datasets contained within suspected disease state 140 training set may include computing a distance value between an item to be classified such as a symptom complaint and each dataset contained within suspected disease state 140 training set which may be represented as a vector. A value of "k" may be pre-determined or selected that will be used for classifications. In an embodiment, value of "k" may be selected as an odd number to avoid a tied outcome. In an embodiment, value of "k" may be decided by KNN module 108 arbitrarily or value may be cross validated to find an optimal value of "k.". KNN module 108 may then select a distance metric that will be used in K-nearest neighbor algorithm 204. In an embodiment, KNN module 108 may utilize Euclidean distance which may be measure distance by subtracting the distance between a training data point and the datapoint to be classified such as symptom complaint datum 112. In an embodiment, Euclidean distance may be calculated by a formula represented as: $E(x,y)=\sqrt{\Sigma_{i=0}^{n}(xi-yi)^2}$. In an embodiment, KNN module 108 may utilize metric distance of cosine similarity which may calculate distance as the difference in direction between two vectors which may be represented as: $similarity = \cos\theta = A \times B \div \|A\|\|B\|$. After selection of "k" value, and selection of distance measurement by KNN module 108, KNN module 108 may partition in "R^N" into sections. Sections may be calculated using the distance metric and the available data points contained within suspected disease state 140 training set. KNN module 108 may calculate a plurality of optimal vector output 136; in such an instance, where a plurality of matching entries are returned, optimal vector output 136 may be obtained by aggregating matching entries including any suitable method for aggregation, including component-wise addition followed by normalization component-wise calculation of arithmetic means, or the like. Optimal vector output 136 may be generated by receiving a user entry containing a datum of user genetic history which may be utilized to update a suspected disease state 140 contained within an optimal vector output 136. For instance and without limitation, a datum of user genetic history that contains one copy of the apolipoprotein E gene may be utilized to select between two optimal vector output 136 whereby a first optimal vector output 136 contains a suspected disease state 140 such as coronary artery disease and a second optimal vector output 136 contains a suspected disease state 140 such as anxiety disorder. In such an instance, datum of user genetic history containing apolipoprotein E gene may be utilized to select optimal vector output 136 containing suspected disease state 140 of coronary artery disease.

Figure 3:
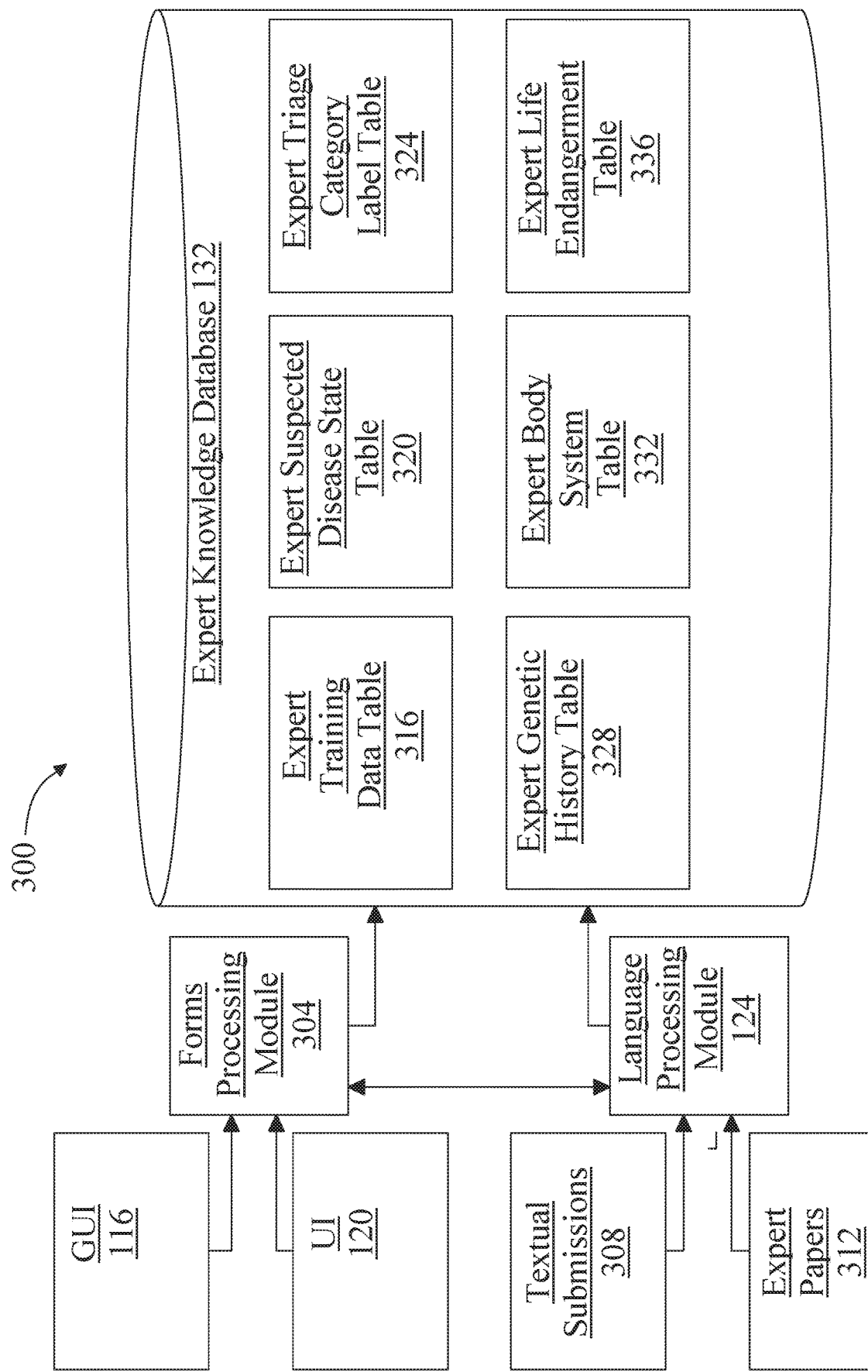
FIG. 3 is a block diagram illustrating an exemplary embodiment of an expert knowledge database.

Referring now to FIG. 3, an exemplary embodiment 300 of expert knowledge database 132 is illustrated. Expert knowledge database 132 may, as a non-limiting example, organize data stored in the expert knowledge database 132 according to one or more database tables. One or more database tables may be linked to one another by, for instance, common column values. For instance, a common column between two tables of expert knowledge database 132 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data may be included in one or more tables.

With continued reference to FIG. 3, expert knowledge database 132 includes a forms processing module 304 that may sort data entered in a submission via graphical user interface 116 and/or user interface 120 by, for instance, sorting data from entries in the first graphical user interface 116 to related categories of data; for instance, data entered in an entry relating in the graphical user interface 116 to a training data set may be sorted into variables and/or data structures for storage of training data sets, while data entered in an entry relating to a category of suspected disease state 140 data and/or an element thereof may be sorted into variables and/or data structures for the storage of, respectively, categories of suspected disease state 140 data. Where data is chosen by an expert from pre-selected entries such as drop-down lists, data may be stored directly; where data is entered in textual form, language processing module 124 may be used to map data to an appropriate existing label, for instance using a vector similarity test or other synonym-sensitive language processing test to map physiological data to an existing label. Alternatively or additionally, when a language processing algorithm, such as vector similarity comparison, indicates that an entry is not a synonym of an existing label, language processing module 124 may indicate that entry should be treated as relating to a new label; this may be determined by, e.g., comparison to a threshold number of cosine similarity and/or other geometric measures of vector similarity of the entered text to a nearest existent label, and determination that a degree of similarity falls below the threshold number and/or a degree of dissimilarity falls above the threshold number. Data from expert textual submissions 308, such as accomplished by filling out a paper or PDF form and/or submitting narrative information, may likewise be processed using language processing module 124. Data may be extracted from expert papers 312, which may include without limitation publications in medical and/or scientific journals, by language processing module 124 via any suitable process as described herein. Persons skilled in the art, upon reviewing the entirety of this disclosure, will be aware of various additional methods whereby novel terms may be separated from already-classified terms and/or synonyms therefore, as consistent with this disclosure.

With continued reference to FIG. 3, one or more database tables in expert knowledge database 132 may include expert training data table 316; expert training data table 316 may contain training data sets such as suspected disease state training data. In an embodiment, suspected disease state training data contained within expert training data table 316 may be organized by symptom complaint, whereby a user entry through graphical user interface 116 and/or user interface 120 containing a symptom complaint may be matched to a symptom complaint contained within expert training data table 316. Suspected disease state training data contained within expert training data table 316 may be received based on expert inputs such as from functional medicine doctors, top journals, papers and the like. One or more database tables in expert knowledge database 132 may include expert suspected disease state table 320; expert suspected disease state 140 table may contain data entries containing symptom complaints experienced by users with particular disease states. For instance and without limitation, expert suspected disease state table 320 may include a suspected disease state 140 such as common cold and symptom complaints experienced by users with the common cold including fever, stuffy nose, watery eyes, sneezing, headache, chills, and body aches. One or more database tables in expert knowledge database 132 may include expert triage category label table 324; expert triage category label table 324 may include information describing particular symptom complaints and/or suspected disease state 140 and associated triage labels. For instance and without limitation, expert triage category label table 324 may include a particular symptom complaint such as chest pain with an associated triage label such as attention in near future. One or more database tables in expert knowledge database 132 may include expert genetic history table 328; expert genetic history table 328 may include entries describing particular genetic history and predisposition for particular disease states. For instance and without limitation, expert genetic history table 328 may include an entry describing breast cancer 1 gene (BRCA 1) and susceptibility to develop breast cancer. One or more database tables in expert knowledge database 132 may include expert body system table 332; expert body system table 332 may include one or more entries describing impact of one or more symptom complaints on one or more body systems. For instance and without limitation, expert body system table 332 may include symptom complaint such as headache impacting the nervous system. One or more database tables in expert knowledge database 132 may include expert life endangerment table 336; expert life endangerment table 336 may include one or more entries describing one or more symptom complaints and effect on life endangerment. For instance and without limitation, expert life endangerment table may include a symptom complaint such as coughing up blood as endangering life.

Figure 4:
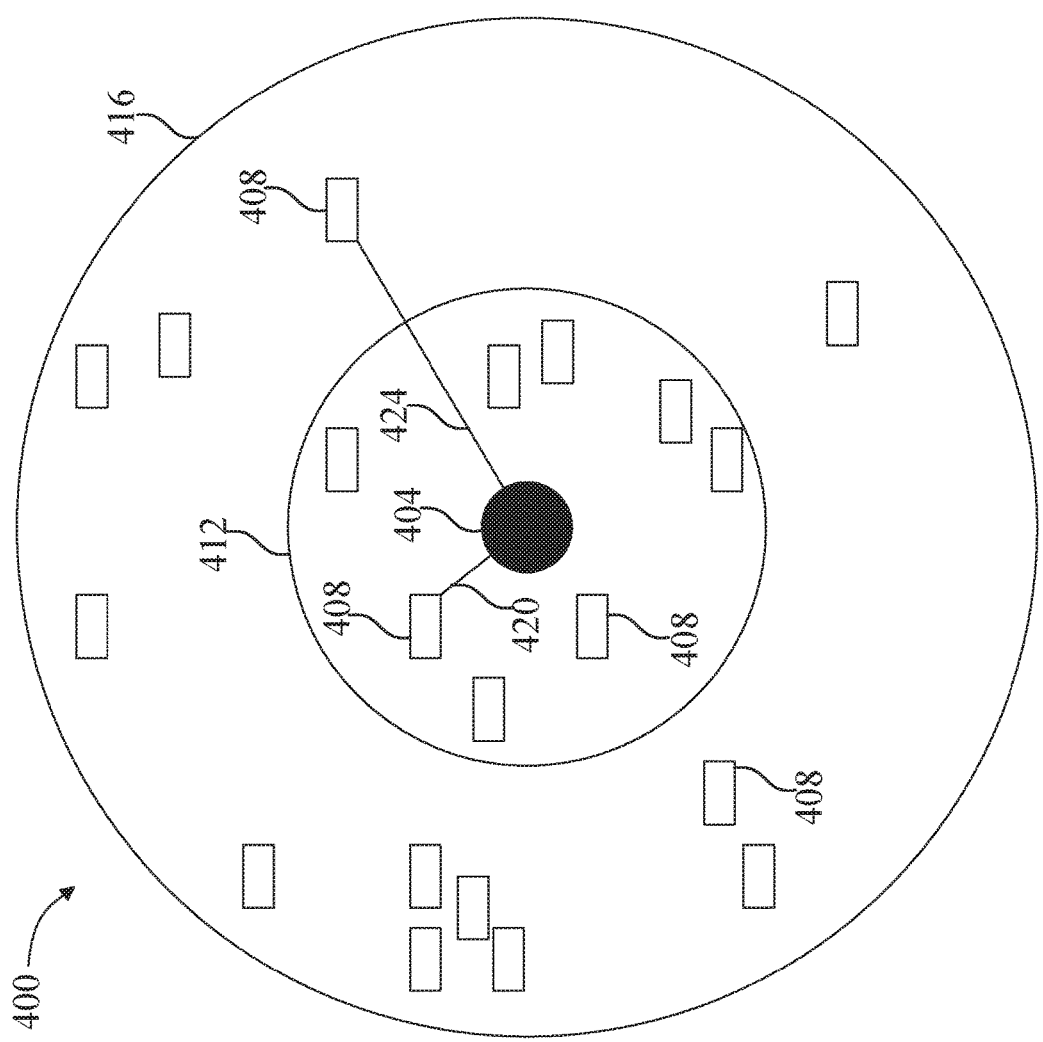
FIG. 4 is a diagrammatic representation of a K-nearest neighbor algorithm.

Referring now to FIG. 4, an exemplary embodiment of graphical representation 400 of k-nearest neighbor algorithm 184 is illustrated. Embodiment 404 represents datapoint to be classified. Datapoint to be classified may include symptom complaint. Embodiment 408 represents data sets from selected suspected disease state training data. Embodiment 408 may be represented as "m" number of datasets contained within suspected disease state training data. Embodiment 412 indicates a first "k" value selected and the corresponding number of datasets contained utilizing first "k" value. Embodiment 416 indicate a second "k" value selected and the corresponding number of datasets contained utilizing second "k" value. Embodiment 420 represents distance between datapoint to be classified embodiment 404 and a particular dataset from suspected disease state training data embodiment 408. Embodiment 424 represents distance between datapoint to be classified embodiment 404 and a particular dataset from suspected disease state training data embodiment 408. Distance may be measured utilizing any of the methodologies as described above in reference to FIG. 2, including for example Euclidean distance and/or cosine similarity.

Figure 5:
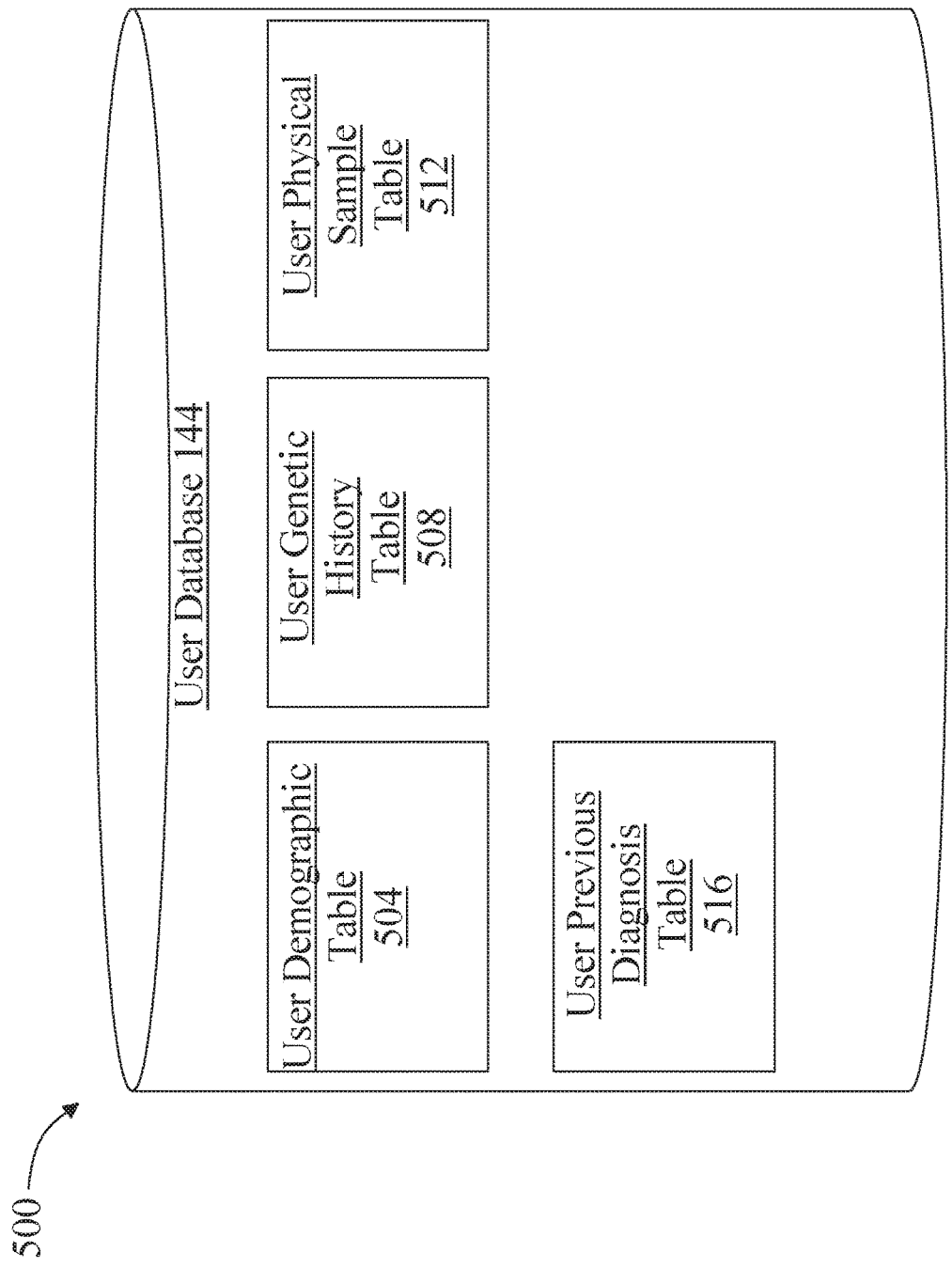
FIG. 5 is a block diagram illustrating an exemplary embodiment of a user database.

Referring now to FIG. 5, an exemplary embodiment 500 of user database 144 is illustrated. One or more database tables in user database 144 may include user demographic table 504; user demographic table may include stored demographic information pertaining to a user. For instance and without limitation, user demographic table 504 may include user contact information, home address, allergies, payment information, marital status, household income, occupation, age, gender, and the like. One or more database tables in user database 144 may include user genetic history table 508; user genetic history table may include stored genetic history data pertaining to a user. For instance and without limitation, user genetic history table 508 may include stored user genetic test results such as a result from a positive test result for the HLA-class II complex gene DQ2 and DQ8 commonly associated with Celiac Disease. One or more database tables in user database 144 may include user physical sample table 512; user physical sample table 512 may include medical history and medical files of various physically extracted samples user may have tested for particular genetic history data. For instance and without limitation, user physical sample table 512 may include a salivary sample analyzed for particular genetic history data and a hair sample analyzed for particular genetic history data. One or more database tables contained within user database 144 may include user previous diagnosis table 516; user previous diagnosis table 516 may include previous medical diagnoses that a user may have received from a medical professional. For instance and without limitation, user previous diagnosis table 516 may include a user's previous diagnoses such as alopecia, hypertension, and prostatitis.

Figure 6:
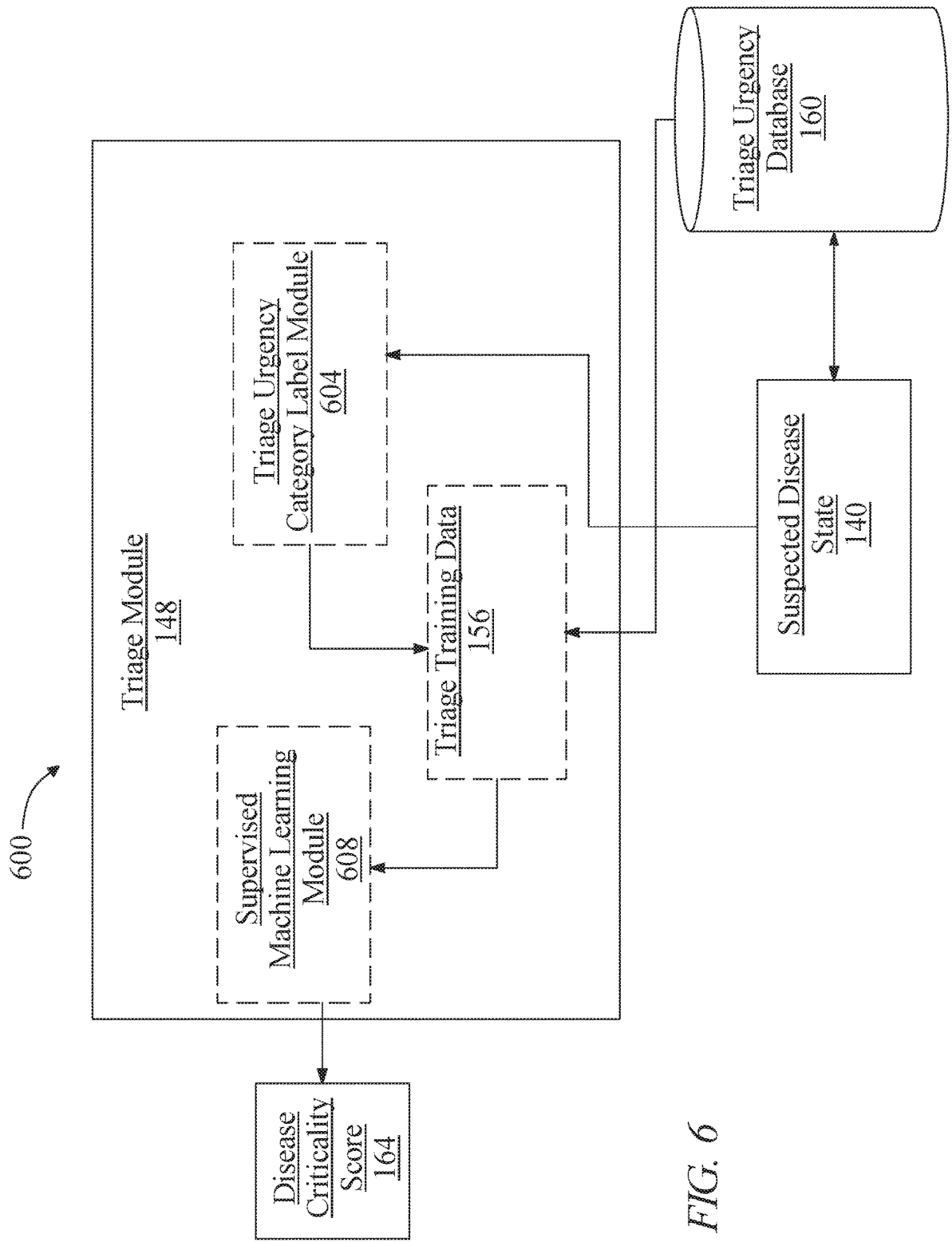
FIG. 6 is a block diagram illustrating an exemplary embodiment of a triage module.

Referring now to FIG. 6, an exemplary embodiment 600 of triage module 148 is illustrated. Triage module 148 may be implemented as a hardware or software module. Triage module 148 is configured to receive an optimal vector output 136 containing a suspected disease state 140 for each of the plurality of symptom complaint datum 112, generate a triage urgency category label 152 for each of the plurality of suspected disease state 140 wherein the triage urgency category label 152 further comprises matching the optimal vector output 136 containing a suspected disease state 140 for each of the plurality of symptom complaint datum 112 to a triage urgency category label 152; select a triage training data 156 as a function of the triage urgency category label 152 for each of the plurality of suspected disease state 140 wherein the triage training data 156 correlates suspected disease state 140 to relative disease criticality scores; generate using a supervised machine-learning processes a disease criticality model that outputs a disease criticality score 164 for each of the plurality of suspected disease state 140 utilizing the selected triage training data 156; evaluate the ranked disease criticality score for each of the plurality of suspected disease state 140 as a function of ranking the disease criticality score 164 for each of the plurality of suspected disease state 140; and display the ranked disease criticality score for each of the plurality of suspected disease state 140 at the graphical user interface 116 operating on the at least a computing device 104.

With continued reference to FIG. 6, triage module 148 receives optimal vector output 136 containing a suspected disease state 140 for each of the plurality of symptom complaint datum 112 from KNN module 108. Triage module 148 may contain a triage urgency category label module 604 that generates a triage urgency category label 152 for each of the plurality of suspected disease state 140. Triage urgency category label module 604 may generate triage urgency category label 152 by matching optimal vector output 136 containing a suspected disease state 140 to a triage urgency category label 152. Triage urgency category label 152 may include any of the triage urgency category label 152 described above in reference to FIG. 1. Triage urgency category label 152 may include immediate attention label when medical attention is needed in less than 1 year, near future label when medical attention is needed in the near future in less than 3 hours, next day label when medical attention is needed in the next day, next week label when medical attention is needed in the next week, check-up label when medical attention is needed at the next scheduled check-up, and self-care label when medical attention is not needed and may be provided at home. Triage urgency category label module 604 may match suspected disease state 140 to triage urgency category label 152 by calculating a triage urgency algorithm. Triage urgency algorithm includes multiplying a body system factor by a life endangerment factor and an alarm condition factor. Factors utilized in calculating triage urgency algorithm are described above in more detail in reference to FIG. 1. In an embodiment, a higher total score for triage urgency algorithm may indicate a higher level of urgency and may cause a suspected disease state 140 to be classified into a more urgent urgency category label such as immediate attention or attention in near future. In an embodiment, a lower total score for triage urgency algorithm may indicate a lower level of urgency and may cause a suspected disease state 140 to be classified into a less urgent urgency category label such as attention in next check-up or self-care. In an embodiment, expert input may guide start and end points for triage urgency algorithm scores to be classified with particular triage urgency labels. Expert input may be received utilizing any of the methods as described above in reference to FIG. 3.

With continued reference to FIG. 6, triage module 148 selects training data as a function of the triage urgency category label 152 for each of the plurality of suspected disease state 140 wherein the triage training data 156 correlates suspected disease state 140 to relative disease criticality scores 164. Triage module 148 may select triage training data 156 from triage urgency database 160. In an embodiment, triage module 148 may select triage training data 156 from triage urgency database 160 by matching a suspected disease state 140 to training data containing the suspected disease state 140 contained within triage urgency database 160 as described in more detail below. For instance and without limitation, triage module 148 may receive an optimal vector output 136 containing a suspected disease state 140 of hypertension. In such an instance, triage module 148 may match suspected disease state 140 of lupus to a training set that contains a data entry of lupus correlated relative disease criticality score for lupus. Triage module 148 may select triage training data 156 by selecting a first triage training set from triage database as a function of triage urgency category label 152. For instance and without limitation, triage module 148 may select triage training data 156 by matching a suspected disease state 140 such as gastritis containing a triage urgency category label 152 of attention in next day to a triage training set located within triage database containing a triage urgency category label 152 of attention in next day. Triage module 148 may then probe the first triage training set to locate a suspected disease state 140. In the aforementioned gastritis example, triage module 148 may probe first triage training set to see if it contains a data entry containing gastritis correlated to a relative disease criticality score. Failing to locate a suspected disease state 140 within a first training set will cause triage module 148 to discard the first training set. Triage module 148 may then select a second triage training set from triage urgency database 160 as a function of a triage urgency category label 152 and probe the second triage training set to locate a suspected disease state 140. Locating a suspected disease state 140 within a second triage training set will allow triage module 148 to select second triage training set to generate an unsupervised machine-learning model. In an embodiment, triage module 148 may continue to select triage training sets from triage urgency database 160 until a suspected disease state 140 is located within a triage training set.

With continued reference to FIG. 6, triage module 148 may include supervised machine-learning module 608. Supervised machine-learning module may generate using a supervised machine-learning model a disease criticality model that outputs a disease criticality score 164 for each of the plurality of suspected disease state 140 utilizing the selected triage training data 156. Supervised machine-learning model outputs a disease criticality score 164 for each of the plurality of suspected disease state 140 utilizing the selected triage training data 156. Supervised machine-learning model may include any of the supervised machine-learning models as described above in reference to FIG. 1. Supervised machine-learning model may utilize suspected disease state 140 as an input and utilize the selected triage training data 156 to output a disease criticality score 164 for the suspected disease state 140. Triage module 148 may evaluate the disease criticality score for each of the plurality of suspected disease state 140 as a function of ranking the disease criticality scores 164 for each of the plurality of suspected disease state 140. Disease criticality score 164 indicates how critical medical attention and/or treatment may be needed for a particular disease. In an embodiment, triage module 148 may rank disease criticality scores 164 in descending order of how critical medical attention may be needed based on disease criticality scores 164. Triage module 148 may evaluate ranked disease criticality score for each of the plurality of suspected disease state 140. Triage module 148 may receive at least a user input datum containing a previous user diagnosis. In an embodiment, triage module 148 may retrieve previous user diagnosis information from user database 144 as described in more detail above in reference to FIG. 5. Triage module 148 may select a suspected disease state 140 as a function of previous user diagnosis and ranked disease criticality score. For instance and without limitation, a previous user diagnosis of ulcerative colitis may be utilized to select a suspected disease state 140 of dehydration as compared to a suspected disease state 140 such as the flu due to known associations with ulcerative colitis and complications that include dehydration. Triage module 148 may display ranked disease criticality score for each of the plurality of suspected disease state 140 at graphical user interface 116 operating on at least a computing device 104.

Figure 7:
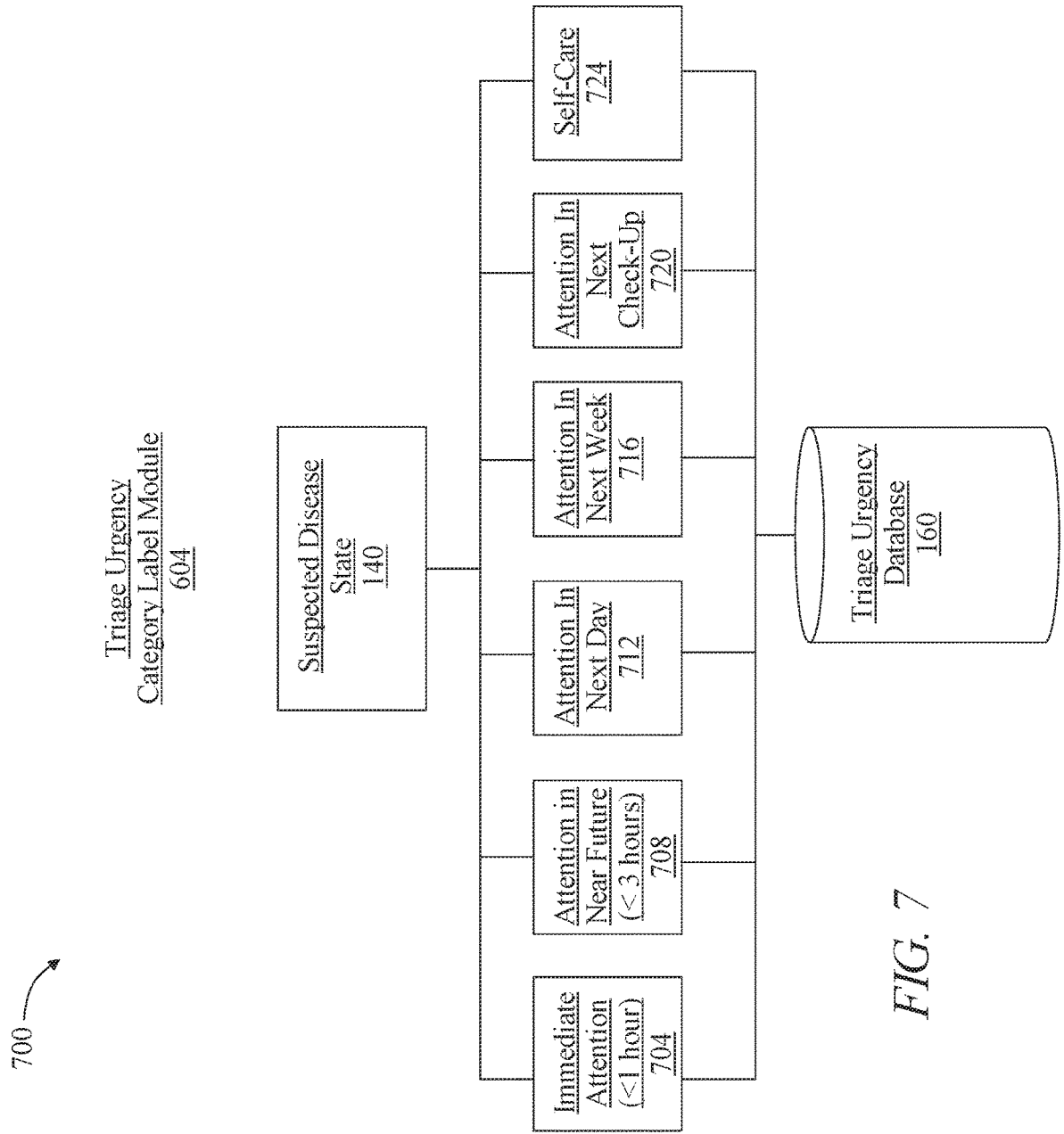
FIG. 7 is a flow diagram illustrating an exemplary flow of triage urgency category label selection.

Referring now to FIG. 7, an exemplary embodiment 700 of triage urgency category label module 604 is illustrated. Triage urgency category label module 604 may receive suspected disease state 140 and classify suspected disease state 140 to a triage urgency category label 152. This may be performed utilizing any of the methodologies as described above in FIG. 1 and FIG. 6. Triage urgency category label 152 may include immediate attention label 704 when medical attention is needed in less than one hour. Triage urgency category label 152 may include attention in near future label 708 when medical attention is needed within the next three hours. Triage urgency category label 152 may include attention in next day label 712 when medical attention is needed within the next twenty four hours. Triage urgency category label 152 may include attention in next week label 716 when medical attention is needed within the next week. Triage urgency category label 152 may include attention in next check-up label 720 when medical attention is needed at the user's next scheduled checkup. Triage urgency category label 152 may include self-care label 724 when medical attention is not needed, and the user can provide treatment himself or herself at home. Selected triage urgency category label 152 may then be utilized by triage module 148 to select triage training data 156 from triage urgency dataset. In an embodiment, triage urgency category label 152 may be matched to triage training sets contained within triage urgency database 160 that are organized according to triage urgency labels.

Figure 8:
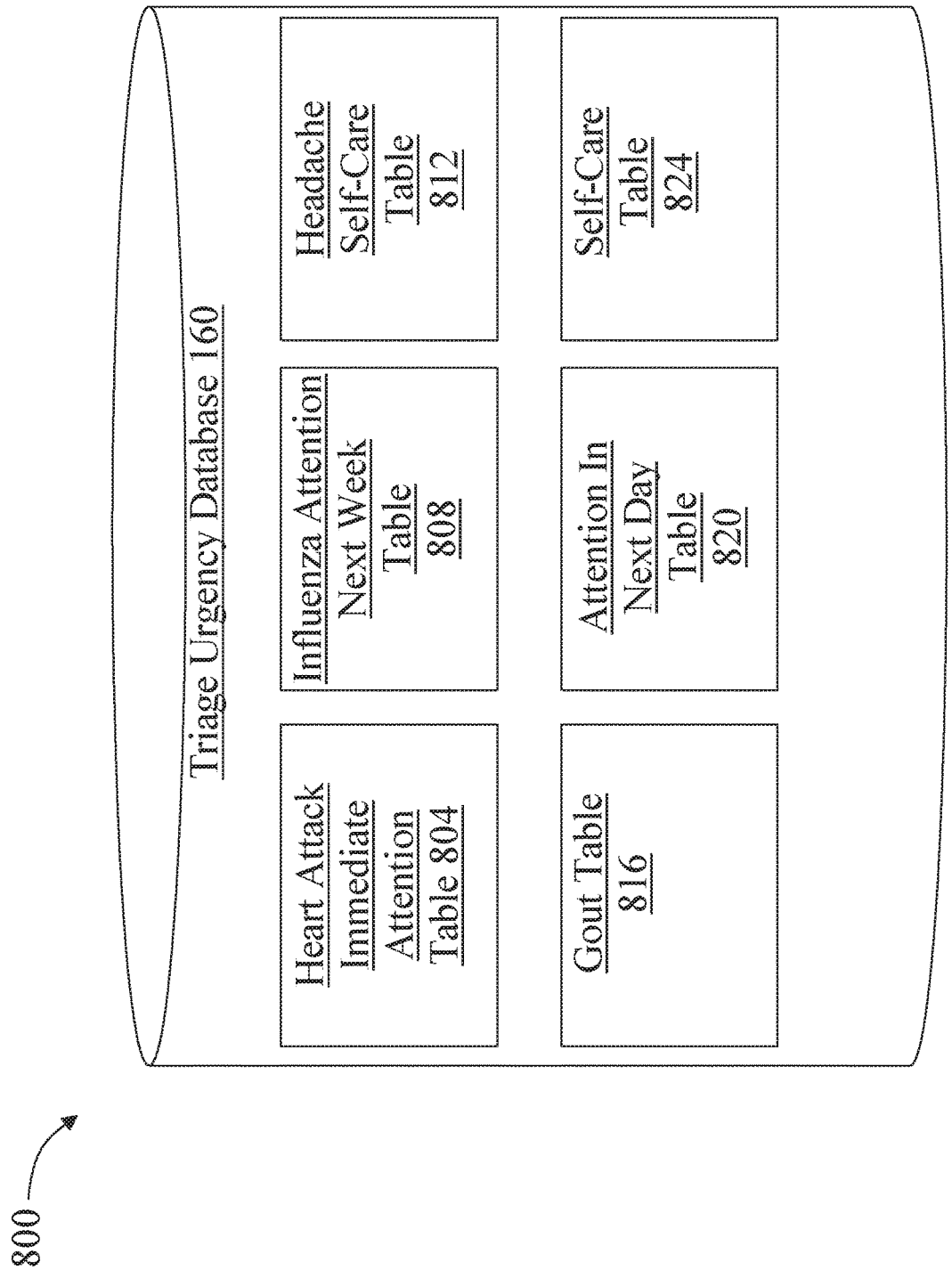
FIG. 8 is a block diagram illustrating an exemplary embodiment of a triage urgency database.

Referring now to FIG. 8, an exemplary embodiment 800 of triage urgency database 160 is illustrated. One or more tables contained within triage urgency database 160 includes heart attack immediate attention table 804; heart attack immediate attention table 804 may include all triage training sets containing heart attack disease state and containing immediate attention triage urgency label. One or more tables contained within triage urgency database 160 may include influenza attention next week table 808; influenza attention next week table 808 may include all triage training sets containing influenza disease state and containing attention next week urgency label. One or more tables contained within triage urgency database 160 may include headache self-are table 812; headache self-care table 812 may include all triage training sets containing headache disease state and containing self-care triage urgency category label 152. One or more tables contained within triage urgency database 160 may include gout table 816; gout table 816 may include all triage training sets containing gout disease state. One or more tables contained within triage urgency database 160 may include attention in next day table 820; attention in next day table 820 may include all triage training sets containing triage urgency category label 152 of attention in next day. One or more tables contained within triage urgency database 160 may include self-care table 824; self-care table 824 may include all triage training sets containing triage urgency category label 152 of self-care.

Figure 9:
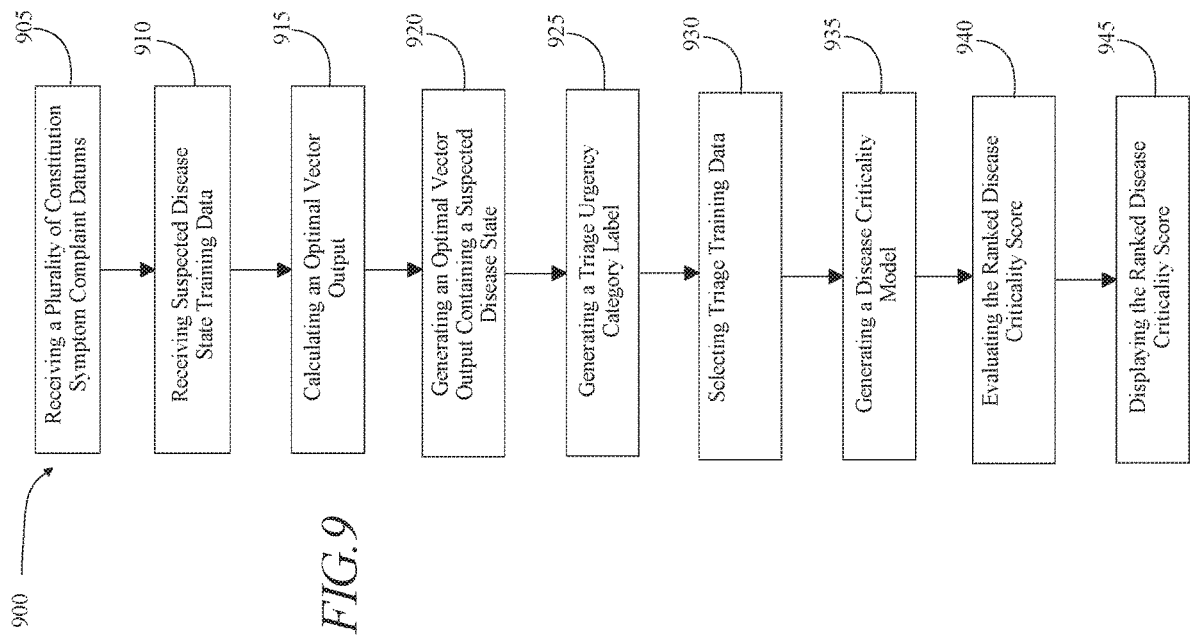
FIG. 9 is a process flow diagram illustrating an exemplary embodiment of a method of prioritizing user symptom complaint inputs.

Referring now to FIG. 9, an exemplary embodiment of a method 900 of prioritizing user symptom complaint inputs. At step 905 a KNN module 108 operating on at least a computing device 104 receives a plurality of symptom complaint datum 112 by a user at a graphical user interface 116 operating on at least a computing device 104. Symptom complaint datum 112 may include any of the constitution complaint datums as described above in reference to FIGS. 1-9. For instance and without limitation, symptom complaint datum 112 may include user generated complaints such as "headache," "back pain," "foot numbness" and "sore ankles." In an embodiment, KNN module 108 receives a plurality of symptom complaint datum 112 generated by a user at a user interface 120 operating on at least a computing device 104. User interface 120 may include any of the user interface 120 as described above in reference to FIG. 1. User interface 120 may be configured to convert oral spoken symptom complaint datum 112 to textual symptom complaint datum 112. This may be done utilizing any of the language processing methods described above in reference to FIG. 1.

With continued reference to FIG. 9, at step 910 a KNN module 108 operating on at least a computing device 104 receives suspected disease state training data correlating at least an element of symptom complaint data to suspected disease state 140 from an expert knowledge database 132 located on at least a computing device 104. KNN module 108 receives suspected disease state training data utilizing any of the methodologies as described above in reference to FIGS. 1-9. Expert knowledge database 132 may include any of the expert knowledge database 132 as described above in reference to FIG. 1 and FIG. 3.

With continued reference to FIG. 9, at step 915 a KNN module 108 operating on at least a computing device 104 calculates an optimal vector output 136 for each of the plurality of symptom complaint datum 112 utilizing a k-nearest neighbor algorithm and the suspected disease state training data. Calculating optimal vector output 136 may be performed utilizing any of the methodologies as described above in reference to FIGS. 1-9. Calculating optimal vector output 136 includes identifying the presence of a symptom complaint datum 112 and confirming a suspected disease state 140. For instance and without limitation, identifying the presence of a symptom complaint datum 112 such as knee pain may be utilized to confirm a suspected disease state 140 such as osteoarthritis. In yet another non-limiting example, identifying the presence of a symptom complaint datum 112 such as muscle twitching may be utilizing to confirm a suspected disease state 140 such as multiple sclerosis. Calculating an optimal vector output 136 includes identifying the presence of a symptom complaint datum 112 and eliminating a suspected disease state 140. For instance and without limitation, a symptom complaint datum 112 such as eye pain may be utilized to eliminate a suspected disease state 140 such as a myocardial infarction. In yet another non-limiting example, a symptom complaint datum 112 such as an earache may be utilized to eliminate a suspected disease state 140 such as foot fungus.

With continued reference to FIG. 9, generating optimal vector output 136 includes displaying optimal vector output 136 containing a suspected disease state 140 to a user, receiving a user entry containing a suspected disease state 140 to the user, receiving a user entry containing a datum of user genetic history, and updating the optimal vector output 136 containing a new suspected disease state 140 as a function of the user entry. User entry containing a datum of user genetic history may be retrieved from user database 144. For instance and without limitation, a user genetic history such as a mutation of the SLC23A1 gene that controls Vitamin C absorption may be utilized to select an updated optimal vector output 136 that includes a suspected disease state 140 of rickets. In yet another non-limiting example, a user genetic history such as a mutation of the GC gene responsible for transporting Vitamin D and showing reduced transportation may be utilized to select an updated optimal vector output 136 that includes a suspected disease state 140 of osteoarthritis.

With continued reference to FIG. 9, calculating optimal vector output 136 includes utilizing k-nearest neighbor algorithm and the suspected disease state training data. This may be performed utilizing any of the methodologies as described above in reference to FIGS. 1-9. K-nearest neighbor algorithm may include any of the k-nearest neighbor algorithms as described above in reference to FIGS. 1-9.

With continued reference to FIG. 9, at step 920 KNN module 108 operating on at least a computing device 104 generates an optimal vector output 136 containing a suspected disease state 140 for each of the plurality of symptom complaint datum 112. Suspected disease state 140 may include any of the suspected disease state 140 as described above in reference to FIGS. 1-9. Triage module 148 operating on at least a computing device 104 receives an optimal vector output 136 for each of the plurality of symptom complaint datum 112.

With continued reference to FIG. 9, at step 925 triage module 148 operating on at least a computing device 104 generates a triage urgency category label 152 for each of the plurality of suspected disease state 140 wherein the triage urgency category label 152 further comprises matching optimal vector output 136 containing a suspected disease state 140 for each of the plurality of symptom compliant datums to a triage urgency category label 152. This may be performed utilizing any of the methodologies as described above in reference to FIGS. 1-9. Triage urgency category label 152 may be generated as a function of calculating a triage urgency algorithm wherein the triage urgency algorithm further comprises multiplying a body system factor by a life endangerment factor and an alarm condition factor. This may be performed utilizing any of the methodologies as described above in reference to FIGS. 1-9. Factors utilized to calculate triage urgency algorithm may include any of the factors as described above in reference to FIGS. 1-9.

With continued reference to FIG. 9, at step 930 triage module 148 operating on at least a computing device 104 selects triage training data 156 as a function of triage urgency category label 152 for each of the plurality of suspected disease state 140 wherein the triage training data 156 correlates suspected disease state 140 to relative disease criticality scores. Triage training data 156 may include any of the triage training data 156 as described above in reference to FIGS. 1-9. Selecting triage training data 156 includes matching a suspected disease state 140 to training data containing the suspected disease state 140 contained within a triage urgency category label 152 database. This may be implemented utilizing any of the methodologies as described above in reference to FIGS. 6-8. Selecting triage training data 156 as a function of the triage urgency category label 152 includes selecting a first triage training set from a triage urgency category label 152 database as a function of the triage urgency category label 152. Triage module 148 probes the first triage training set to locate a suspected disease state 140 and failing to locate the suspected disease state 140 within the first triage training set discards the first triage training set. Triage module 148 selects a second triage training set from the triage urgency category label 152 database as a function of the triage urgency category label 152. Triage module 148 probes the second triage training set to locate a suspected disease state 140 and locating the suspected disease state 140 within the second triage training set. Triage module 148 selects the second triage training set. In an embodiment, triage module 148 may continue to select training sets until a training set contains a suspected disease state 140. For instance and without limitation, triage module 148 may select and discard seven triage training sets before selecting an eight training set containing the suspected disease state 140. Triage training sets may be classified and organized by suspected disease type and/or triage urgency category label 152 as described above in more detail in FIG. 8.

With continued reference to FIG. 9, at step 935 triage module 148 operating on at least a computing device 104 generates using a supervised machine-learning model a disease criticality model that outputs a disease criticality score for each of the plurality of suspected disease state 140 utilizing the selected triage training data 156. Generating supervised machine-learning model may be done utilizing any of the methodologies as described above in reference to FIGS. 1-9. Disease criticality score may include any of the disease criticality scores as described above in reference to FIGS. 1-9. Disease criticality score may include an intervention score, a constitutional expert score, and an alternative treatment score, which may be calculated utilizing any of the methodologies as described above in reference to FIG. 1.

With continued reference to FIG. 9, at step 940 triage module 148 operating on at least a computing device 104 evaluates the ranked disease criticality score for each of the plurality of suspected disease state 140 as a function of ranking the disease criticality score for each of the plurality of suspected disease state 140, receiving at least a user input datum wherein the at least a user input datum further comprises a previous user diagnosis, selecting a suspected disease state 140 as a function of the previous user diagnosis and the ranked disease criticality score; and displaying the selected suspected disease state 140 at the graphical user interface 116 operating on the at least a computing device 104. For instance and without limitation, triage module 148 may receive a previous user diagnosis such as rheumatoid arthritis which may be utilized to select a suspected disease state 140 such as hypothyroidism due to a link of both being autoimmune diseases as compared to selecting a suspected disease state 140 such as fatigue. Previous user diagnosis may be useful to select a suspected disease state 140 when a plurality of suspected disease state 140 may contain similar disease criticality scores.

With continued reference to FIG. 9, at step 945 triage module 148 operating on at least a computing device 104 displays ranked disease criticality score for each of the plurality of suspected disease state 140 at the graphical user interface 116 operating on at least a computing device 104.

It is to be noted that any one or more of the aspects and embodiments described herein may be conveniently implemented using one or more machines (e.g., one or more computing device 104 that are utilized as a user computing device 104 for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device 104) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device 104) and any related information (e.g., data structures and data) that causes the machine to perform any one of the methodologies and/or embodiments described herein.

Examples of a computing device 104 include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device 104 may include and/or be included in a kiosk.

Figure 10:
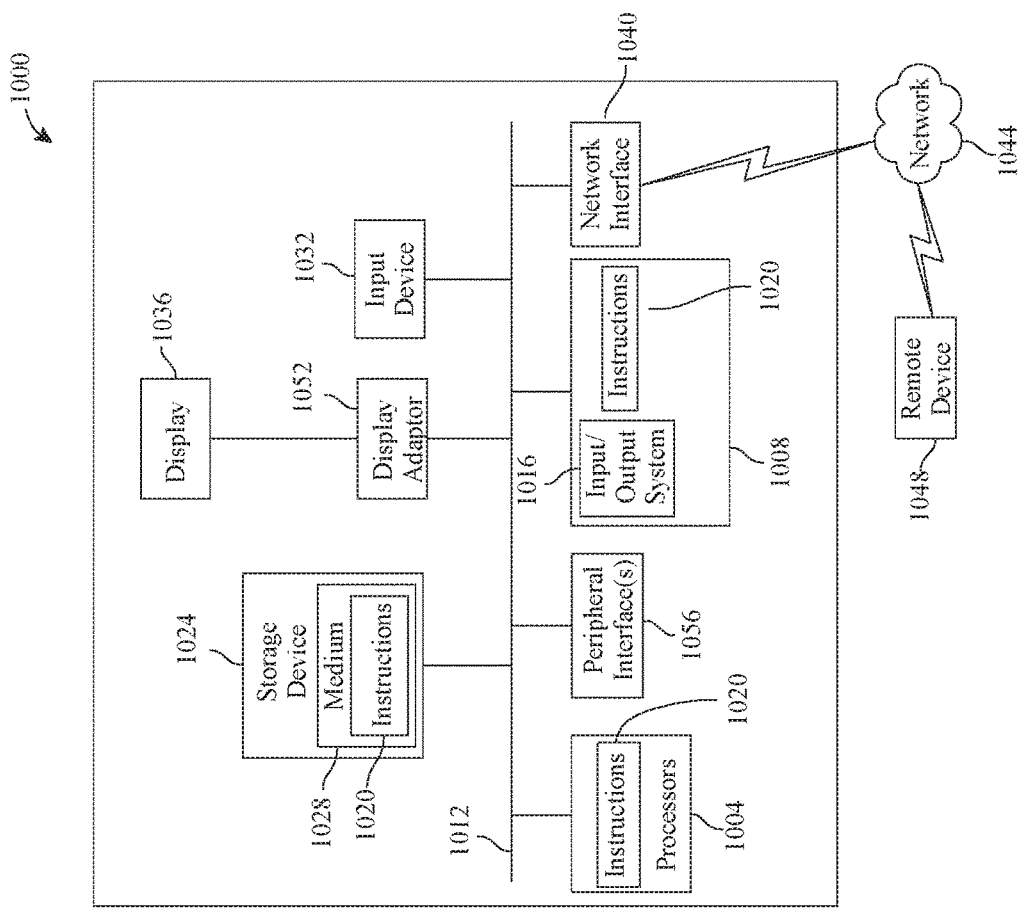
FIG. 10 is a block diagram of a computing system that can be used to implement any one or more of the methodologies disclosed herein and any one or more portions thereof.

FIG. 10 shows a diagrammatic representation of one embodiment of a computing device 104 in the exemplary form of a computer system 1000 within which a set of instructions for causing a control system to perform any one or more of the aspects and/or methodologies of the present disclosure may be executed. It is also contemplated that multiple computing device 104 may be utilized to implement a specially configured set of instructions for causing one or more of the devices to perform any one or more of the aspects and/or methodologies of the present disclosure. Computer system 1000 includes a processor 1004 and a memory 1008 that communicate with each other, and with other components, via a bus 1012. Bus 1012 may include any of several types of bus structures including, but not limited to, a memory bus, a memory controller, a peripheral bus, a local bus, and any combinations thereof, using any of a variety of bus architectures.

Memory 1008 may include various components (e.g., machine-readable media) including, but not limited to, a random access memory component, a read only component, and any combinations thereof. In one example, a basic input/output system 1016 (BIOS), including basic routines that help to transfer information between elements within computer system 1000, such as during start-up, may be stored in memory 1008. Memory 1008 may also include (e.g., stored on one or more machine-readable media) instructions (e.g., software) 1020 embodying any one or more of the aspects and/or methodologies of the present disclosure. In another example, memory 1008 may further include any number of program modules including, but not limited to, an operating system, one or more application programs, other program modules, program data, and any combinations thereof.

Computer system 1000 may also include a storage device 1024. Examples of a storage device (e.g., storage device 1024) include, but are not limited to, a hard disk drive, a magnetic disk drive, an optical disc drive in combination with an optical medium, a solid-state memory device, and any combinations thereof. Storage device 1024 may be connected to bus 1012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1024 (or one or more components thereof) may be removably interfaced with computer system 1000 (e.g., via an external port connector (not shown)). Particularly, storage device 1024 and an associated machine-readable medium 1028 may provide nonvolatile and/or volatile storage of machine-readable instructions, data structures, program modules, and/or other data for computer system 1000. In one example, software 1020 may reside, completely or partially, within machine-readable medium 1028. In another example, software 1020 may reside, completely or partially, within processor 1004.

Computer system 1000 may also include an input device 1032. In one example, a user of computer system 1000 may enter commands and/or other information into computer system 1000 via input device 1032. Examples of an input device 1032 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1032 may be interfaced to bus 1012 via any of a variety of interfaces (not shown) including, but not limited to, a serial interface, a parallel interface, a game port, a USB interface, a FIREWIRE interface, a direct interface to bus 1012, and any combinations thereof. Input device 1032 may include a touch screen interface that may be a part of or separate from display 1036, discussed further below. Input device 1032 may be utilized as a user selection device for selecting one or more graphical representations in a graphical interface as described above.

A user may also input commands and/or other information to computer system 1000 via storage device 1024 (e.g., a removable disk drive, a flash drive, etc.) and/or network interface device 1040. A network interface device, such as network interface device 1040, may be utilized for connecting computer system 1000 to one or more of a variety of networks, such as network 1044, and one or more remote devices 1048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing device 104, and any combinations thereof. A network, such as network 1044, may employ a wired and/or a wireless mode of communication. In general, any network topology may be used. Information (e.g., data, software 1020, etc.) may be communicated to and/or from computer system 1000 via network interface device 1040.

Computer system 1000 may further include a video display adapter 1052 for communicating a displayable image to a display device, such as display device 1036. Examples of a display device include, but are not limited to, a liquid crystal display (LCD), a cathode ray tube (CRT), a plasma display, a light emitting diode (LED) display, and any combinations thereof. Display adapter 1052 and display device 1036 may be utilized in combination with processor 1004 to provide graphical representations of aspects of the present disclosure. In addition to a display device, computer system 1000 may include one or more other peripheral output devices including, but not limited to, an audio speaker, a printer, and any combinations thereof. Such peripheral output devices may be connected to bus 1012 via a peripheral interface 1056. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for prioritizing user symptom complaint inputs the system comprising:
    at least a computing device, wherein the at least a computing device further comprises one or more network interfaces, a non-volatile memory, and one or more processors;
    a K-nearest neighbors (KNN) module operating on the at least a computing device, the KNN module designed and configured to:
        receive a plurality of symptom complaint datums generated by a user at a graphical user interface operating on the at least a computing device;
        receive from an expert knowledge database located on the at least a computing device, suspected disease state training data correlating at least an element of symptom complaint data to suspected disease states;
        calculate an optimal vector output for each of the plurality of symptom complaint datums utilizing a k-nearest neighbor algorithm and the suspected disease state training data; and
        generate an optimal vector output containing a suspected disease state for each of the plurality of symptom complaint datums; and
    a triage module operating on the at least a computing device the triage module designed and configured to:
        receive the optimal vector output containing a suspected disease state for each of the plurality of symptom complaint datums;
        generate a triage urgency category label for each of the plurality of suspected disease states wherein the triage urgency category label further comprises matching the optimal vector output containing a suspected disease state for each of the plurality of symptom complaint datums to a triage urgency category label;
        select triage training data as a function of the triage urgency category label for each of the plurality of suspected disease states wherein the triage training data correlates suspected disease states to relative disease criticality scores;
        generate using a supervised machine-learning model a disease criticality model that inputs each of the plurality of suspected disease states and outputs a disease criticality score as a function of the selected triage training data, wherein each of the plurality of suspected disease states is generated by a lazy-learning process and a risk function representing an expected loss;
        evaluate the disease criticality score for each of the plurality of suspected disease states as a function of ranking the disease criticality score for each of the plurality of suspected disease states; and
        display the ranked disease criticality score for each of the plurality of suspected disease states at the graphical user interface.

2. The system of claim 1, wherein the KNN module is further configured to receive a plurality of symptom complaint datums generated by a user at a user interface operating on the at least a computing device wherein the user interface is designed and configured to generate speech-to-text algorithms to transform spoken symptom complaint datums into text symptom complaint datums.

3. The system of claim 1, wherein calculating an optimal vector output further comprises:
    identifying the presence of a symptom complaint datum; and
    confirming a suspected disease state.

4. The system of claim 1, wherein calculating an optimal vector output further comprises:
    identifying the presence of a symptom complaint datum; and
    eliminating a suspected disease state.

5. The system of claim 1, wherein generating an optimal vector output further comprises:
    displaying the optimal vector output containing a suspected disease state to the user;
    receiving a user entry containing a datum of user genetic history; and
    updating the optimal vector output containing a new suspected disease state as a function of the user entry.

6. The system of claim 1, wherein the triage urgency category label is generated as a function of calculating a triage urgency algorithm wherein the triage urgency algorithm further comprises multiplying a body system factor by a life endangerment factor, and by an alarm condition factor.

7. The system of claim 1, wherein selecting triage training data as a function of the triage urgency category label further comprises matching a suspected disease state to triage training data containing the suspected disease state contained within a triage urgency database.

8. The system of claim 1, wherein selecting triage training data as a function of the triage urgency category label further comprises:
    selecting a first triage training set from a triage urgency database as a function of the triage urgency category label;
    probing the first triage training set to locate a suspected disease state and failing to locate the suspected disease state within the first triage training set;
    discarding the first triage training set;
    selecting a second triage training set from the triage urgency database as a function of the triage urgency category label;
    probing the second triage training set to locate a suspected disease state and locating the suspected disease state within the second triage training set; and
    selecting the second triage training set.

9. The system of claim 1, wherein evaluating the ranked disease criticality score for each of the plurality of suspected disease states further comprises:
    receiving at least a user input datum wherein the at least a user input datum further comprises a previous user diagnosis;
    selecting a suspected disease state as a function of the previous user diagnosis and the ranked disease criticality score; and
    displaying the selected suspected disease state at the graphical user interface operating on the at least a computing device.

10. The system of claim 1, wherein the disease criticality score further comprises an intervention score, a constitutional expert score, and an alternative treatment score.

11. A method of prioritizing user symptom complaint inputs the system comprising:
- receiving by at least a computing device a plurality of symptom complaint datums generated by a user at a graphical user interface operating on the at least a computing device;
- receiving by the at least a computing device a suspected disease state training data correlating at least an element of symptom complaint data to suspected disease states from an expert knowledge database located on the at least a computing device;
- calculating by the at least a computing device an optimal vector output for each of the plurality of symptom complaint datums utilizing a k-nearest neighbor algorithm and the suspected disease state training data;
- generating by the at least a computing device an optimal vector output containing a suspected disease state for each of the plurality of symptom complaint datums;
- generating by the at least a computing device a triage urgency category label for each of the plurality of suspected disease states wherein the triage urgency category label further comprises matching the optimal vector output containing a suspected disease state for each of the plurality of symptom complaint datums to a triage urgency category label;
- selecting by the at least a computing device a triage training data as a function of the triage urgency category label for each of the plurality of suspected disease states wherein the triage training data correlates suspected disease states to relative disease criticality scores;
- generating by the at least a computing device using a supervised machine-learning model a disease criticality model that inputs each of the plurality of suspected disease states and outputs a disease criticality score for each of the plurality of suspected disease states as a function of the selected triage training data, wherein each of the plurality of suspected disease states are generated by a lazy-learning process and a scoring risk function representing an expected loss;
- evaluating by the at least a computing device the disease criticality score for each of the plurality of suspected disease states as a function of ranking the disease criticality score for each of the plurality of suspected disease states; and
- displaying by the at least a computing device the ranked disease criticality score for each of the plurality of suspected disease states at the graphical user interface operating on the at least a computing device.

12. The method of claim 11, wherein receiving a plurality of symptom complaint datums further comprises receiving a plurality of symptom complaint datums generated by a user at a user interface operating on the at least a computing device wherein the user interface generates speech-to-text algorithms to transform spoken symptom complaint datums into text symptom complaint datums.

13. The method of claim 11, wherein calculating an optimal vector output further comprises:
- identifying the presence of a symptom complaint datum; and
- confirming a suspected disease state.

14. The method of claim 11, wherein calculating an optimal vector output further comprises:
- identifying the presence of a symptom complaint datum; and
- eliminating a suspected disease state.

15. The method of claim 11, wherein generating an optimal vector output further comprises:
- displaying the optimal vector output containing a suspected disease state to the user;
- receiving a user entry containing a datum of user genetic history; and
- updating the optimal vector output containing a new suspected disease state as a function of the user entry.

16. The method of claim 11, wherein the triage urgency category label is generated as a function of calculating a triage urgency algorithm wherein the triage urgency algorithm further comprises multiplying a body system factor by a life endangerment factor, and by an alarm condition factor.

17. The method of claim 11, wherein selecting triage training data as a function of the triage urgency category label further comprises matching a suspected disease state to triage training data containing the suspected disease state contained within a triage urgency database.

18. The method of claim 11, wherein selecting triage training data as a function of the triage urgency category label further comprises:
- selecting a first triage training set from a triage urgency database as a function of the triage urgency category label;
- probing the first triage training set to locate a suspected disease state and failing to locate the suspected disease state within the first triage training set;
- discarding the first triage training set;
- selecting a second triage training set from the triage urgency database as a function of the triage urgency category label;
- probing the second triage training set to locate a suspected disease state and locating the suspected disease state within the second triage training set; and
- selecting the second triage training set.

19. The method of claim 11, wherein evaluating the ranked disease criticality score for each of the plurality of suspected disease states further comprises:
- receiving at least a user input datum wherein the at least a user input datum further comprises a previous user diagnosis;
- selecting a suspected disease state as a function of the previous user diagnosis and the ranked disease criticality score; and
- displaying the selected suspected disease state at the graphical user interface operating on the at least a computing device.

20. The method of claim 11, wherein the disease criticality score further comprises an intervention score, a constitutional expert score, and an alternative treatment score.

* * * * *